United States Patent
Haj-Ahmad

(10) Patent No.: US 12,005,438 B2
(45) Date of Patent: Jun. 11, 2024

(54) SAMPLE COLLECTION APPARATUS AND USES THEREOF

(71) Applicant: Norgen Biotek Corp., Thorold (CA)

(72) Inventor: Yousef Haj-Ahmad, St. Catharines (CA)

(73) Assignee: Norgen Biotek Corp., Thorold (CA)

( * ) Notice: Subject to any disclaimer, the term of this patent is extended or adjusted under 35 U.S.C. 154(b) by 163 days.

(21) Appl. No.: 17/474,185

(22) Filed: Sep. 14, 2021

(65) Prior Publication Data

US 2022/0080404 A1    Mar. 17, 2022

Related U.S. Application Data

(60) Provisional application No. 63/078,605, filed on Sep. 15, 2020.

(51) Int. Cl.
*A61B 10/00* (2006.01)
*B01L 3/00* (2006.01)

(52) U.S. Cl.
CPC ......... *B01L 3/502* (2013.01); *B01L 2200/025* (2013.01); *B01L 2200/026* (2013.01);
(Continued)

(58) Field of Classification Search
CPC ................. B01L 3/502; B01L 2200/16; B01L 2200/025; B01L 2200/0026;
(Continued)

(56) References Cited

U.S. PATENT DOCUMENTS

| 3,684,455 A | 8/1972 | Vacirca et al. |
| 5,020,690 A | 6/1991 | Kishikawa et al. |

(Continued)

FOREIGN PATENT DOCUMENTS

| EP | 3782554 A1 | 2/2021 |
| KR | 20200011802 A | 2/2020 |

(Continued)

OTHER PUBLICATIONS

Galior, Kornelia D., et al. "Challenges with At-home and Mail-in Direct-to-Consumer Testing", Clinics in Laboratory Medicine, vol. 40, No. 1, pp. 25-36 (2020).
(Continued)

*Primary Examiner* — Jill A Warden
*Assistant Examiner* — Michael Stanley Gzybowski
(74) *Attorney, Agent, or Firm* — COATS & BENNETT, PLLC

(57) ABSTRACT

An apparatus for collecting and combining a sample, and in particular, a biological sample, with a reagent, and uses thereof. The apparatus comprises a sample collection container and a complementary sealing cap. A sealed reagent reservoir containing a reagent, such as a preservative reagent, is provided in a lower portion of the collection container. A piercing insert is nested within the collection container, above the seal of the reagent reservoir. Following the collection of the sample into the collection container, the action of sealing the collection container with the cap causes the piercing insert to engage with and disrupt the seal on the reagent reservoir, thereby exposing the collected sample to the reagent.

23 Claims, 14 Drawing Sheets

(52) U.S. Cl.
CPC ... *B01L 2200/0689* (2013.01); *B01L 2200/16* (2013.01); *B01L 2300/042* (2013.01); *B01L 2300/044* (2013.01); *B01L 2300/046* (2013.01); *B01L 2300/0672* (2013.01)

(58) Field of Classification Search
CPC ......... B01L 2200/0689; B01L 2300/16; B01L 2300/042; B01L 2300/044; B01L 2300/46; B01L 2300/0672
See application file for complete search history.

(56) References Cited

U.S. PATENT DOCUMENTS

| | | | |
|---|---|---|---|
| 5,022,288 A * | 6/1991 | Taktakian | B67B 7/18 81/3.4 |
| 5,827,675 A | 10/1998 | Skiffington et al. | |
| 5,965,453 A | 10/1999 | Skiffington et al. | |
| 6,180,395 B1 | 1/2001 | Skiffington et al. | |
| 6,634,243 B1 | 10/2003 | Wickstead et al. | |
| 7,225,689 B2 | 6/2007 | Wickstead et al. | |
| 7,257,991 B2 | 8/2007 | Wickstead et al. | |
| 7,645,424 B2 | 1/2010 | O'Donovan | |
| 8,173,388 B2 | 5/2012 | Pasmore et al. | |
| 8,221,381 B2 | 7/2012 | Muir et al. | |
| 8,617,487 B2 | 12/2013 | Plante et al. | |
| 8,642,323 B2 | 2/2014 | Sharpin | |
| 8,802,034 B2 | 8/2014 | Bartfeld et al. | |
| 8,932,539 B2 | 1/2015 | Plante et al. | |
| 9,056,317 B2 | 6/2015 | Bartfeld et al. | |
| 9,138,747 B2 | 9/2015 | Williams et al. | |
| 9,149,807 B2 | 10/2015 | Niggel et al. | |
| 9,207,164 B2 | 12/2015 | Muir et al. | |
| 9,260,740 B2 | 2/2016 | Sharpin | |
| 9,403,164 B2 | 8/2016 | Williams et al. | |
| 9,442,046 B2 | 9/2016 | Biadillah et al. | |
| 9,468,925 B2 | 10/2016 | Bartfeld et al. | |
| 9,687,843 B2 | 6/2017 | Bartfeld et al. | |
| 9,726,585 B2 | 8/2017 | Jakobsen et al. | |
| 9,732,376 B2 | 8/2017 | Oyler et al. | |
| 9,757,095 B2 | 9/2017 | Terbrueggen et al. | |
| 9,932,629 B2 | 4/2018 | Hopper | |
| 9,975,684 B1 | 5/2018 | Dvorak | |
| 10,005,599 B2 | 6/2018 | Friesen et al. | |
| 10,189,020 B2 | 1/2019 | Williams et al. | |
| 10,376,247 B2 | 8/2019 | Jakobsen et al. | |
| 10,463,347 B2 | 11/2019 | Terbrueggen et al. | |
| 10,525,473 B2 | 1/2020 | Williams | |
| 10,549,272 B2 | 2/2020 | Bartfeld et al. | |
| 10,576,468 B2 | 3/2020 | Biadillah et al. | |
| 10,597,207 B2 | 3/2020 | Seelhofer | |
| 2005/0167296 A1 | 8/2005 | Shenkar et al. | |
| 2007/0183937 A1 | 8/2007 | Sarstedt | |
| 2010/0113976 A1* | 5/2010 | Wahl | B01L 3/50825 220/254.1 |
| 2010/0121046 A1 | 5/2010 | Ahlquist et al. | |
| 2011/0168659 A1 | 7/2011 | Hsieh | |
| 2013/0092690 A1 | 4/2013 | Skakoon | |
| 2013/0164738 A1 | 6/2013 | Becker et al. | |
| 2015/0251176 A1 | 9/2015 | Becker et al. | |
| 2015/0353249 A1 | 12/2015 | Muir et al. | |
| 2016/0265022 A1 | 9/2016 | Yang-Woytowitz et al. | |
| 2017/0224315 A1 | 8/2017 | Bastia | |
| 2017/0246625 A1 | 8/2017 | Becker et al. | |
| 2017/0265847 A1 | 9/2017 | Cortelazzo | |
| 2018/0153522 A1 | 6/2018 | Terbrueggen et al. | |
| 2018/0193830 A1 | 7/2018 | Nishikawa et al. | |
| 2018/0272330 A1 | 9/2018 | Lee et al. | |
| 2018/0272331 A1 | 9/2018 | Choi et al. | |
| 2019/0094114 A1 | 3/2019 | Myers, III et al. | |
| 2019/0142395 A1 | 5/2019 | Bartelucci | |
| 2020/0022684 A1 | 1/2020 | Sessions et al. | |
| 2020/0079559 A1 | 3/2020 | Bangera et al. | |
| 2020/0156076 A1 | 5/2020 | Crescenzi et al. | |
| 2020/0261066 A1 | 8/2020 | Sessions et al. | |

FOREIGN PATENT DOCUMENTS

| | | |
|---|---|---|
| WO | 2018078516 A1 | 5/2018 |
| WO | 2019238263 A1 | 12/2019 |
| WO | 2020108802 A1 | 6/2020 |

OTHER PUBLICATIONS

Salivanti, Francesa, et al., "The pre-analytical phase of the liquid biopsy", New Biotechnology, vol. 55, pp. 19-29 (2020).

Langie, S.A.S., et al., "Whole-genome saliva and blood DNA methylation profiling in individuals with a respiratory allergy", PLoS One vol. 11, No. 3: e0151109 (2016).

Maria, N.I., et al., "MxA as a clinically applicable biomarker for identifying systemic interferon type I in primary Sjogren's syndrome", Ann. Rheum. Dis., vol. 73, pp. 1052-1059 (2014).

* cited by examiner

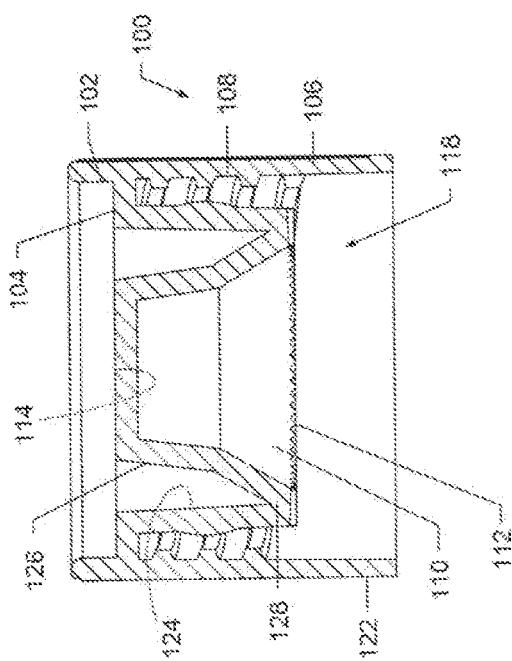
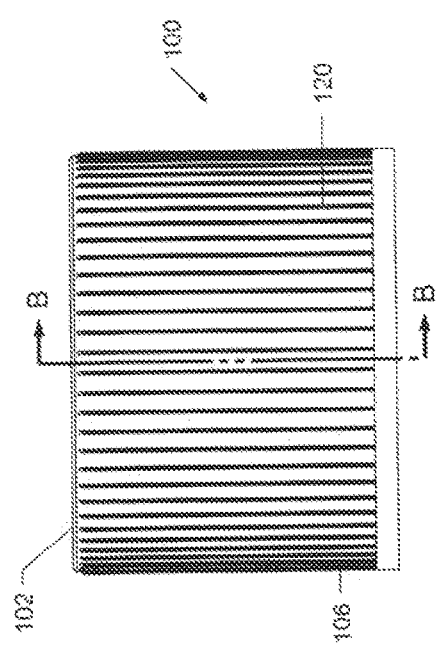
Figure 8
Figure 7

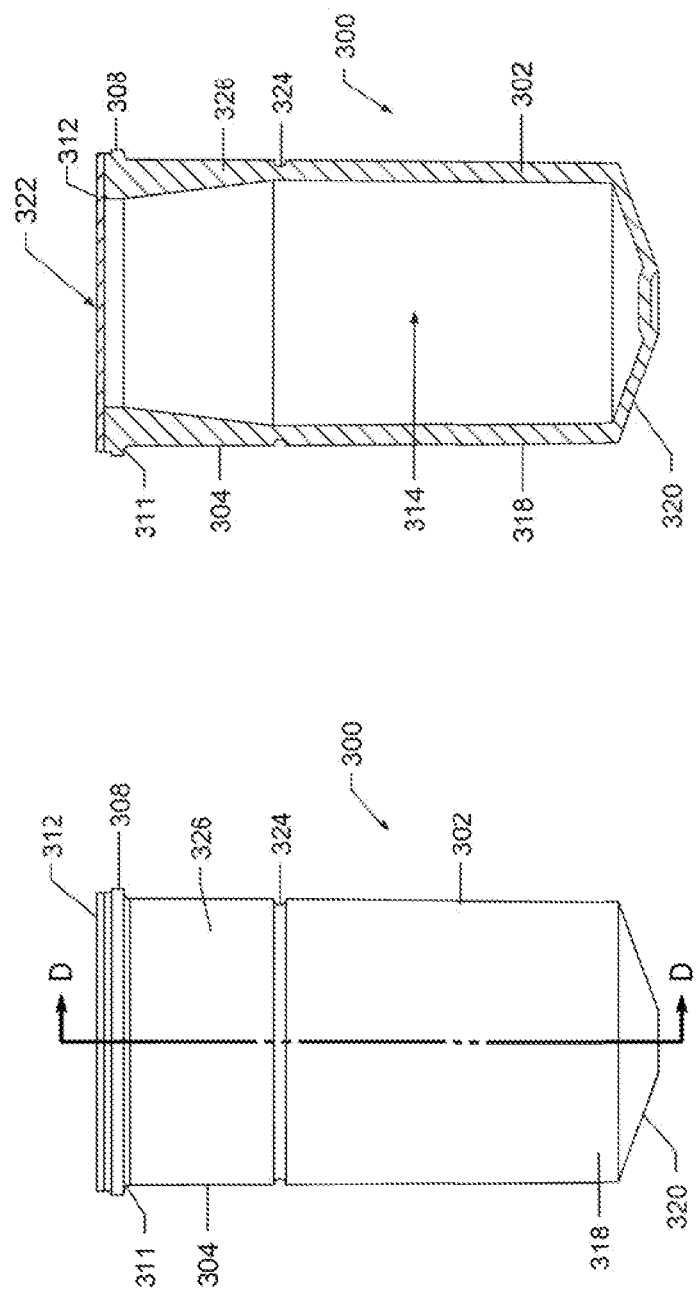

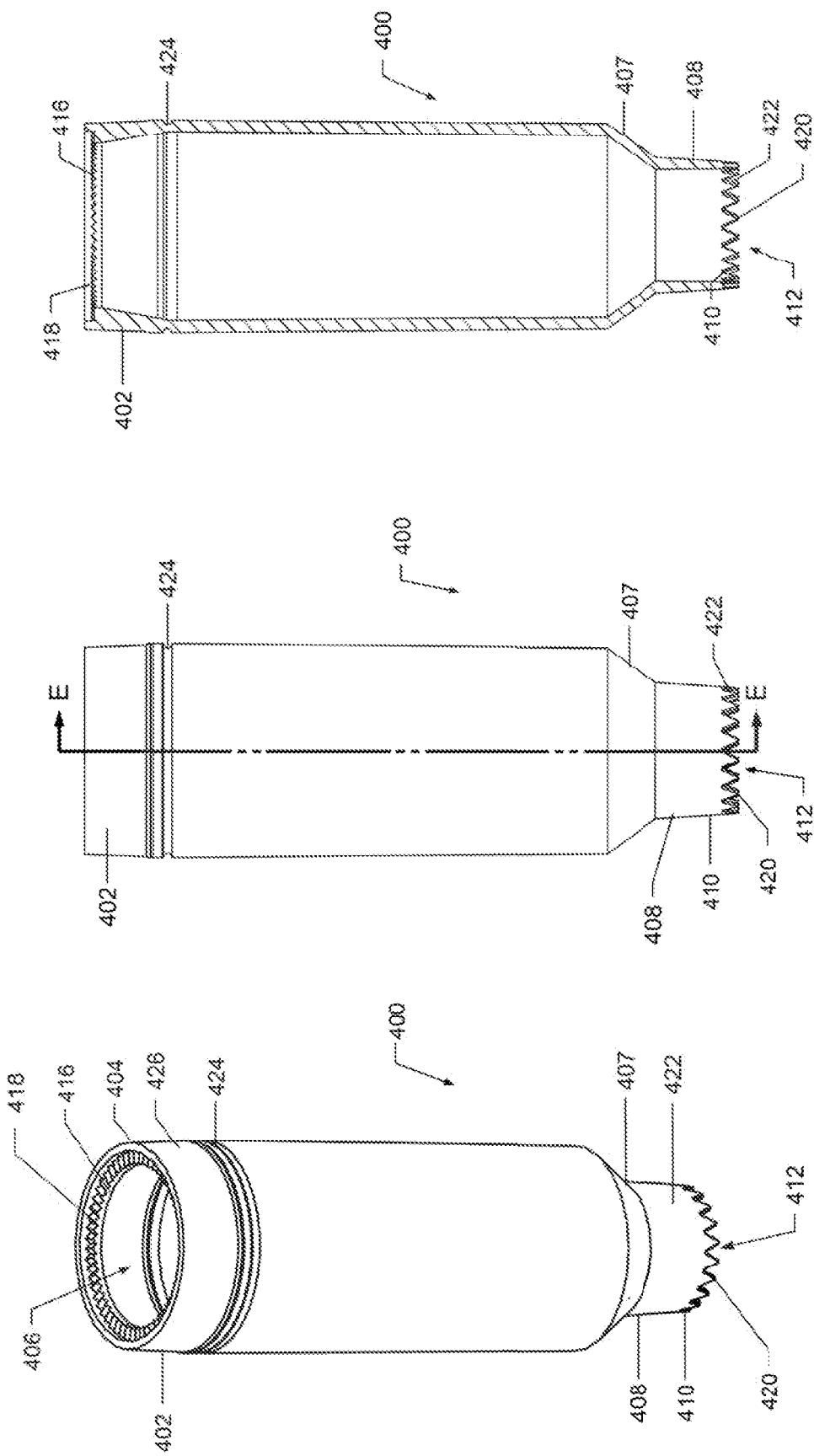

SAMPLE COLLECTION APPARATUS AND USES THEREOF

CROSS REFERENCE TO RELATED APPLICATIONS

This application claims priority from U.S. provisional application No. 63/078,605, filed Sep. 15, 2020, the entirety of which is hereby incorporated by reference.

FIELD OF INVENTION

The present invention relates to an apparatus for collecting and combining a sample with a reagent and uses thereof, and in particular, use for the collection and preservation of a biological sample.

BACKGROUND

The ability to obtain clinically relevant data from biological samples is a powerful tool in in vitro molecular diagnostics, prognostics, and therapeutics. Significant improvements of downstream assays and data analyses have been made in recent years. However, it was found that preanalytical variables, such as sample handling, stabilization and transport can have a severe impact on the utility of the clinical data derived from these samples (Galior et al., 2020; Salivanti et al., 2020). Effective sample collection and stabilization requires easy-to-use sample collection devices that can be utilized properly and quickly regardless of the user's technical expertise.

Another variable that confounds the interpretation of clinical data is the complexity of the sample collection device and procedure. For instance, non-invasive sampling (e.g. saliva and stool) and can be performed by patients themselves or untrained caregivers making these sample types a convenient substitute of blood, especially for long-term monitoring (e.g. therapeutic drugs monitoring) or for screening a large number of patients (Langie et al., 2016), as well as the development of point-of-care diagnostics (Maria et al., 2014).

There are a number of different collection and preservation devices and systems available on the market for collecting biological samples and adding preservative to the collected samples. In some of these devices the stabilizing agents are held separately from the collection device itself. With these devices, a user will collect a biological sample into a receiving vessel, and then the user will open the separate container holding the preservative (e.g. dose ampule) and combine it with the biological sample. While such containers and systems do work, there are a number of risks associated with these types of systems, including the fact that the user must handle the dose ampule and deal with disposing of the ampule after the stabilizing agent has been added. Often these are chemical-based preservatives, making this a risk for home-use and point-of-care applications. Furthermore, as these types of devices rely on the user ensuring that the preservative is added to the sample, there is user error and risk associated with individuals who may not properly add the preservative, or who may spill some of the preservative or who may not add the preservative at all.

Ideal collection and preservation systems, particularly ones for at home use, should be easy to use, not require extensive instructions and should be designed in such a way that failures of the device will be minimized or eliminated all together. Ideally, the device should be designed in such a way that when it is closed or assembled to seal in the biological sample the preservative will automatically be added to the collected sample and therefore the risk associated with the user having to add this separately will be eliminated. Furthermore, the device should be designed to be compatible with standard automation machines for the isolation of the DNA or RNA from the preserved sample, as often many samples are processed at the same time and therefore automation is used. In addition, the device should not be overly complicated to manufacture, as this will interfere with mass production of the devices.

SUMMARY OF INVENTION

The present invention generally relates to an apparatus for collecting and combining a sample with a reagent and uses thereof.

In one aspect of the present invention, provided is an apparatus for collecting and combining a sample with a reagent, the apparatus comprising: a container comprising an upper portion defining an opening for receiving the sample and a closed, lower portion comprising a cavity for containing the sample and a reservoir containing the reagent, the reservoir comprising a pierceable membrane; a cap configured to removably engage the container to form a seal, the cap comprising first engagement means; and an insert configured to nest within the container, the insert comprising an upper portion defining an upper opening, the upper portion comprising second engagement means complementary to the first engagement means; and a lower portion defining a lower opening, the lower portion comprising one or more piercing elements; the insert being movable from a first position to a second position within the container, wherein when the insert is in the first position, the one or more piercing elements are located above the pierceable membrane; and wherein when said apparatus is sealed by removable engagement of the container with the cap, the first engagement means engage with the second engagement means causing the insert to move downward within the container from the first position to the second position, whereby the one or more piercing elements disrupt the pierceable membrane to allow fluid communication between the cavity and the reservoir.

In one embodiment, the cap comprises a top portion and a skirt, the skirt comprising internal threads configured to engage with external threads provided on the upper portion of the container to removably engage the container with the cap when the internal threads are screwed onto the external threads.

In a further embodiment, the first engagement means extend from an underside portion of the cap into the interior of the cap.

In a further embodiment, the first engagement means comprise a first plurality of teeth and the second engagement means comprise a second plurality of teeth, wherein the first plurality of teeth are configured to engage the second plurality of teeth to affect downward movement of the insert within the container when the cap is engaged with the container.

In a further embodiment, the insert comprises a plurality of piercing elements and a lower peripheral edge of the insert is in the form of a serrated edge.

In a further embodiment, the reservoir is in the form of a capsule, the capsule comprising a cavity for containing the reagent and an opening which is sealed with the pierceable membrane, and wherein the capsule is configured to be received in the lower portion of the container.

In a further embodiment, the reservoir is in the form of a capsule, and the capsule comprises a skirt extending from a peripheral edge of the capsule, the skirt configured to abut the interior surface of the lower portion of the container.

In a further embodiment, the reservoir is in the form of a capsule, and the capsule comprises a skirt extending from a peripheral edge of the capsule and a first peripheral retaining lip extending from the interior surface of the lower portion of container, the skirt configured to abut the first peripheral retaining lip.

In a further embodiment, the reservoir is in the form of a capsule, and the capsule further comprises an annular groove defined on an exterior surface of the capsule, and a second peripheral retaining lip extending from the interior surface of the lower portion of the container, the second peripheral retaining lip configured to be received within the annular groove of the capsule.

In a further embodiment, the insert further comprises an annular groove defined on an exterior surface of the insert, and a peripheral retaining lip extending from the interior surface of the upper portion of the container, the retaining lip configured to be received within the annular groove of the insert.

In a further embodiment, the apparatus further comprises a funnel configured to be placed over or be received within the upper portion of the container, wherein the funnel has an upper open end for receiving the sample and a lower open end in fluid communication with the container.

In a further embodiment, the container is a tube. The tube may comprise a false bottom extending from the lower portion of the tube.

In a further embodiment, the reagent is a preservative reagent. The preservative reagent may be a nucleic acid preservative agent, such as is a DNA preservative reagent and/or an RNA preservative reagent.

In accordance with another aspect of the present invention, provided is a method for collecting and combining a sample with a reagent, the method comprising: providing the apparatus of the present invention; adding the sample into the container; and closing said apparatus by removably engaging the cap with the container, whereby said insert is moved downward within the container from the first position to the second position, disrupting the pierceable membrane to expose the sample to the reagent.

In an embodiment, the pierceable membrane of the reservoir is substantially removed from the reservoir by the one or more piercing elements.

In a further embodiment, the reagent is a preservative reagent. The preservative reagent may be a nucleic acid preservative agent, such as is a DNA preservative reagent and/or an RNA preservative reagent.

In a further embodiment, the sample is a biological sample.

In a further embodiment, the biological sample is a liquid biological sample. The liquid biological sample may be blood, plasma, serum, urine, fecal matter, tears, sweat, saliva, breast milk, amniotic fluid, seminal fluid, cerebral spinal fluid, or colostrum sample, and in particular, the liquid biological sample may be a saliva sample.

In a further embodiment, the biological sample is a solid biological sample. The solid biological sample may be a tissue sample or a stool sample.

In accordance with another aspect of the present invention, provided is a kit for collecting and combining a sample with a reagent, the kit comprising the apparatus of the present invention, and instructions for the use thereof.

In an embodiment, the sample is a saliva sample, and the reagent is a DNA preservative reagent and/or an RNA preservative reagent and wherein the kit further comprises a funnel.

In a further embodiment, the sample is a stool sample, and the reagent is a DNA preservative reagent and/or an RNA preservative reagent and wherein the kit further comprises a stool collecting device, wherein the stool collecting device is a spoon or a spatula.

BRIEF DESCRIPTION OF THE DRAWINGS

Preferred embodiments of the invention will now be described, by way of example, with reference to the accompanying drawings, in which:

FIG. 7 is a side view of the cap depicted in FIG. 5;

FIG. 8 is a cross-sectional view of the cap taken along line B-B in FIG. 7;

FIG. 14 is a side view of the reagent reservoir depicted in FIG. 1;

FIG. 15 is a cross-sectional view of the reagent reservoir taken along line D-D in FIG. 14;

FIG. 16 is a perspective view of a first embodiment of the insert depicted in FIG. 1;

FIG. 17 is a side view of the insert depicted in FIG. 16;

FIG. 18 is a cross-sectional view of the insert taken along line E-E in FIG. 17;

Similar references are used in different figures to denote similar components.

DESCRIPTION

As will be discussed in more detail below, the present invention provides a sample collection apparatus for collecting and combining a sample with a reagent. The sample collection apparatus of the present invention comprises a sealable sample container containing a desired reagent, that can be used to overcome the drawbacks associated with other systems available on the market. The present invention is configured to streamline the sample collection process such that once the sample has been collected in the sample container, the act of snapping or twisting a cap in place will simultaneously seal the sample container for safe transport and dispense the desired reagent, such as a preservative reagent, thereby removing any additional user steps for separately adding the reagent. In addition, the sample container of the present invention can be sized and configured to be compatible with standard automation machines, such as automated nucleic acid isolation systems. Accordingly, use of the sample collection apparatus of the present invention may be a particular benefit for users who are processing large numbers of samples.

Apparatus for Collecting and Combining a Sample with a Reagent

Figure 1:
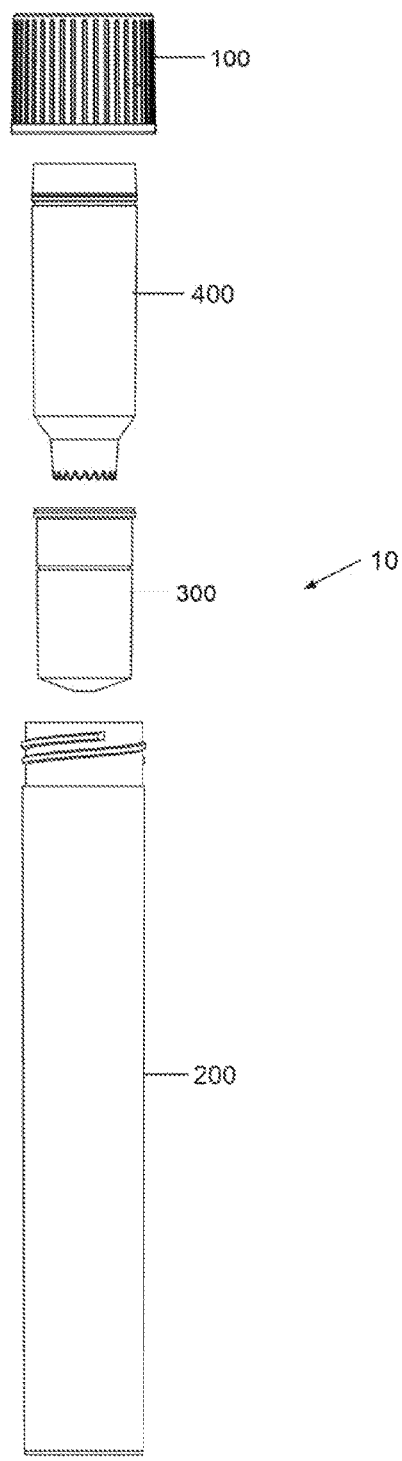
FIG. 1 is an exploded view of an apparatus for collecting and combining a sample with a reagent in accordance with one embodiment of the present invention, showing a cap, insert, reagent reservoir in capsule form, and sample container in the form of a collection tube.

In one aspect, provided is an apparatus for collecting a sample, such as a biological sample, and for combining the sample with a desired reagent, such as a preservative reagent. As shown in FIG. 1, in one embodiment, the apparatus 10 comprises a sample container in the form of a collection tube 200 for containing a sample, preferably a biological sample, and a removable cap 100 for sealing the tube 200 once the sample has been collected into the tube 200. The apparatus 10 further comprises a reagent reservoir 300. As more clearly shown in FIG. 4, the reagent reservoir 300 is contained in a lower portion 204 of the tube. In one embodiment, the reagent reservoir 300 may be in the form of a capsule or a pod, as shown in FIG. 1, comprising a pierceable membrane or film sealing the reagent within the capsule or pod. The apparatus further comprises a piercing insert 400, which is nested within the tube 200 and above the reagent reservoir 300. In use, the action of sealing the tube 200 with the cap 100, (for example, by twisting the cap 100 onto the tube 200) results in the piercing insert 300 moving downward within tube 200 and disrupting the pierceable membrane or film of the reservoir 300, thereby exposing the collected sample to the reagent.

Sample Container

The sample collection apparatus of the present invention comprises a sealable sample container for containing a collected sample and an appropriate reagent to be combined with collected sample. The sample container can be a variety of sizes and shapes as determined by the needs and preferences of the user. Preferably, the sample container is in the form of a collection tube to facilitate subsequent processing of the collected sample.

Figure 4:
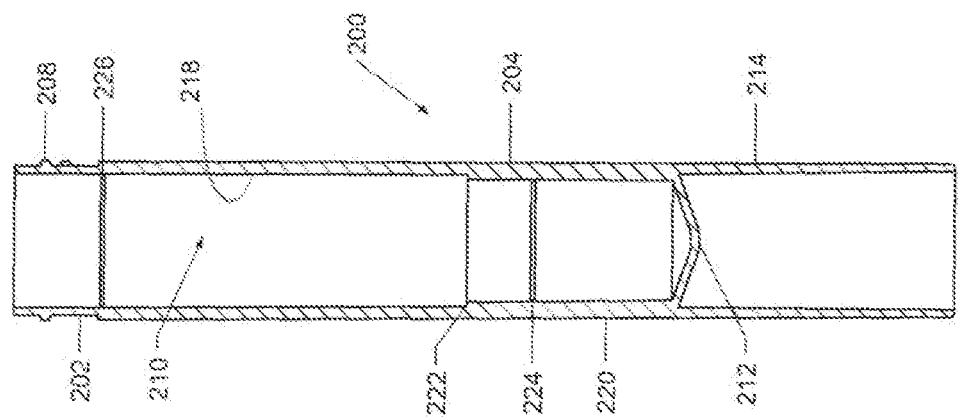
FIG. 4 is a cross-sectional view of the collection tube taken along line A-A in FIG. 3.
Figure 3:
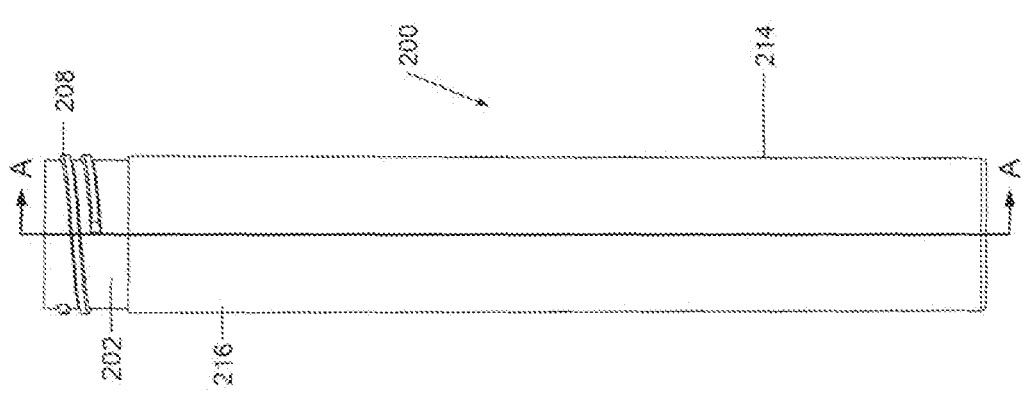
FIG. 3 is a side view of the collection tube depicted in FIG. 1.
Figure 2:
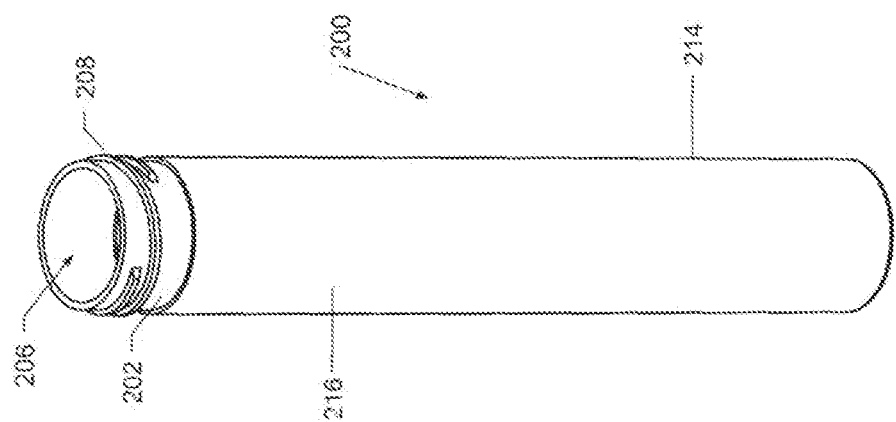
FIG. 2 is a perspective view of the collection tube depicted in FIG. 1.

As shown in FIGS. 2, 3 and 4, in one embodiment, the sample container is a collection tube 200, which may be generally cylindrical in shape. The tube 200 comprises an open upper portion 202 defining an opening 206 for receiving a sample, preferably a biological sample, and a closed lower portion 204 capable of housing a reservoir 300 containing a reagent, preferably a preservative reagent. The size and shape of the tube 200 can be varied depending on the type and amount of sample to be collected and the manner in which the sample will be stored and/or processed following collection. In particular, when used in the collection of biological samples, the shape and size of the tube 200 may be configured for ease of use with conventional, automated nucleic acid isolation systems. For example, for use with common automated systems, the tube 200 may be about 92 mm (ca. 9 cm) in height and about 16.2 mm (ca. 1.6 cm) in width.

The upper portion 202 of the tube 200 defines an opening 206 for receiving the sample. As shown in FIGS. 2, 3 and 4, the respective internal diameters of the upper and lower portions 202, 204 of the tube 200 may be similarly sized. In further embodiments, it may be desirable to have an upper portion 202 which is wider than the rest of the tube 200, to provide a larger opening 206 to ease collection of the sample.

Figure 6:
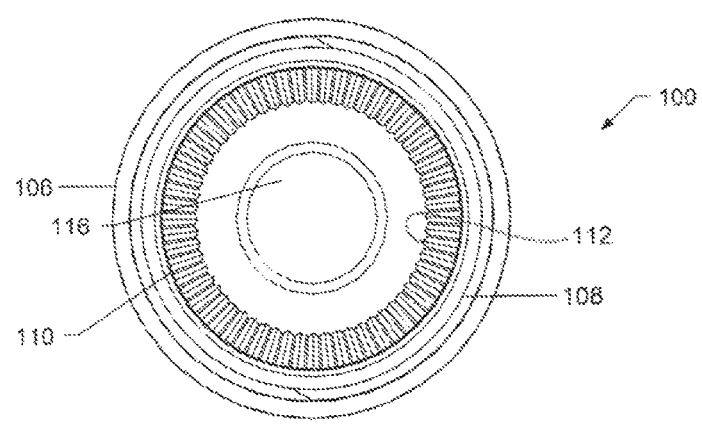
FIG. 6 is plan view of the underside of the cap depicted in FIG. 5.
Figure 10:
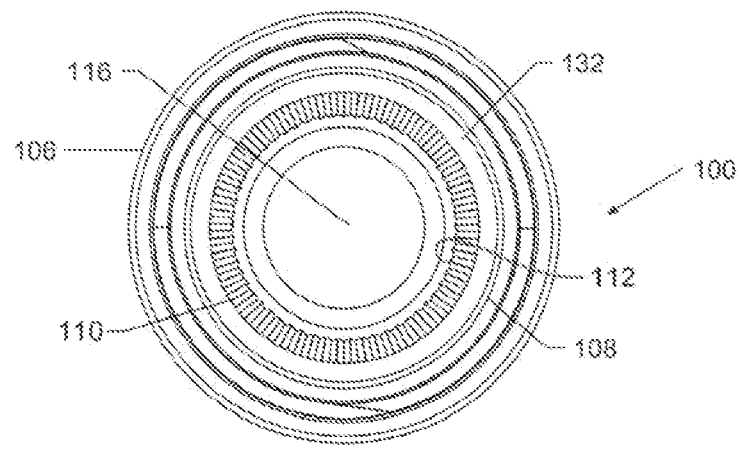
FIG. 10 is plan view of the underside of the cap depicted in FIG. 9.

The tube 200 and cap 100 may be provided with complementary threads 208 and 108 or other suitable engagement means to facilitate removably engaging the cap 100 with the tube 200 to seal the apparatus 10 once the sample has been collected. As shown in FIGS. 2, 3 and 4, the upper portion 202 of the tube 200 may be provided with a plurality of external threads 208, which mate with complementary internal threads 108 provided inside the cap 100 as shown in FIGS. 6 and 8, which illustrate a first embodiment of the cap, and in FIGS. 10 and 12, which illustrate a second embodiment of the cap. Preferably, the internal and external threads 108 and 208 are complementary helical threads. To removably engage the cap 100 with the tube 200, the internal threads 108 can be screwed onto the external threads 208 to form a seal between the cap 100 and the tube 200, preferably an airtight or fluid tight seal. As will be discussed in greater detail below, in a preferred embodiment, the twisting action of threading the cap 100 onto the tube 200 will result in the piercing insert 400 being rotated downward within the tube 200.

The interior of the tube 200 comprises a cavity 210, which is sized and configured to contain the reagent reservoir 300, the piercing insert 400 and the collected sample. The tube 200 and its corresponding cavity 210 can be sized to accommodate a variety of different types and amounts of samples, including but not limited to biological samples, food and beverage samples, environmental samples, and chemical samples, and the requisite amounts of the appropriate reagent. For example, the tube 200 and its corresponding cavity 210 can be sized to accommodate a variety of different types and amounts of biological samples, including liquid biological samples and solid biological samples, and the requisite amounts of the appropriate reagent, preferably a preservative reagent, for the particular biological sample. In one embodiment, the biological sample may be a saliva sample. In such embodiments, the cavity 210 may be sized to accommodate between about 1 ml to about 3 ml of the saliva sample and about 1 ml to about 2 ml of an appropriate reagent, preferably a preservative reagent, such as a nucleic acid preservative reagent, with the total volume of the cavity 210 being about 9 ml. In another embodiment, the biological sample may be a stool sample. In such embodiments, the cavity 210 may be sized to accommodate between about 100 mg to about 1 g of the stool sample and about 1 ml to about 2 ml of the appropriate reagent, preferably a preservative reagent, such as a nucleic acid preservative reagent.

The lower portion 204 of the tube 200 is closed. The shape of the closed end 212 can be varied depending on the type and amount of sample to be collected and the manner in which the sample will be stored and/or processed following collection. For example, the tube 200 may have a round or conical shaped bottom to facilitate sample handling processes involving centrifugation steps.

The reagent reservoir 300 is seated within the lower portion 204 of the tube 200. The lower portion 204 of the tube may be provided with a first retaining lip 222 extending peripherally from an interior surface 218 of the tube 200 to assist in seating the reagent reservoir 300 within the tube 200 and a second retaining lip 224, which engages with a corresponding annular groove 324 defined in the reagent reservoir 300 (see FIGS. 13A, 13B, 14, and 15) to prevent the reagent reservoir 300 from being dislodged once the reagent reservoir 300 has been seated within the lower portion 204 of the tube 200. As shown in FIG. 4, in one embodiment, the first retaining lip or flange 222 may be formed by increasing the wall thickness 220 in the lower portion 204 of the tube, thereby reducing the internal diameter of the lower portion 204 relative to the rest of the tube 200. Alternatively, the first retaining lip 222 may be formed as an annular structure extending from the interior surface of the lower portion 204 of the tube. The second retaining lip 224 can be similarly formed as the first retaining lip 222. As shown in FIG. 4, the second retaining lip 224 may be formed as an annular structure extending from the interior surface of the lower portion 204 of the tube.

The piercing insert 400 is nested within the cavity 210 of the tube 200 and positioned above the pierceable membrane 312 of the reagent reservoir 300. To prevent the piercing insert 400 from accidently falling out of the tube 200 during use and to prevent premature movement of the piercing insert 400 within the tube 200 prior to capping the tube 200, the tube 200 may be provided with a further retaining lip 226 as shown in FIG. 4, which engages with an annular groove 424 defined on an exterior surface 426 of the piercing insert 400 (see FIGS. 19-21). This further retaining lip 226 may be formed as an annular structure extending from the interior surface of the upper portion 202 of the tube.

To allow the tube 200 to be self-standing and to facilitate use of the apparatus in automated processes and systems, the tube 200 may optionally comprise a false bottom 214 as shown in FIGS. 2, 3, and 4. The false bottom 214 may be in the form of a generally cylindrical sleeve extending from the lower portion 204 of the tube 200.

The exterior surface 216 of the tube 200 may be provided with indicia (not shown) to facilitate the use of the apparatus 10. For example, the tube 200 may be provided with a fill-line indicia or other measurement indicia to ensure that the correct amount of sample is collected into the tube. The tube 200 may also be provided with labels or writing areas on the exterior surface to facilitate identification of the tube 200. In particular, the tube 200 may be provided with a bar code (e.g. printed directly on the tube or provided as a label affixed to the tube) to facilitate identification, especially for use of the apparatus 10 in high volume, automated systems.

The tube 200 may be made of any suitable material, which is compatible with the sample to be collected and the subsequent storage and processing of the sample. For example, for use in the collection of biological samples, preferably, the tube 200 may be of a suitable plastic material, including, but not limited to: polyethylene, such as high-density polyethylene (HDPE), medium-density polyethylene (MDPE), low-density polyethylene (LDPE) and linear low-density polyethylene (LLDPE); polypropylene; polystyrene; and polycarbonate. In a more preferred embodiment, the tube is made from polypropylene and can be manufactured using conventional methods, such as injection molding.

Sealing Cap

The sample collection apparatus of the present invention further comprises a cap for sealing the sample container, following the collection of the sample into the sample container. Preferably, the sealing cap forms an airtight or fluid tight seal when the cap is engaged with the sample container. Disposed within the interior of the cap are first engagement means, which are capable of interacting with second engagement means extending from an upper portion of the piercing insert. When the cap is snapped or twisted onto the sample container, the first engagement means is lowered into the sample container and engages with the second engagement means, which causes the piercing insert to move downwards within the sample container and to disrupt the pierceable membrane or film of the reagent reservoir.

Figure 5:
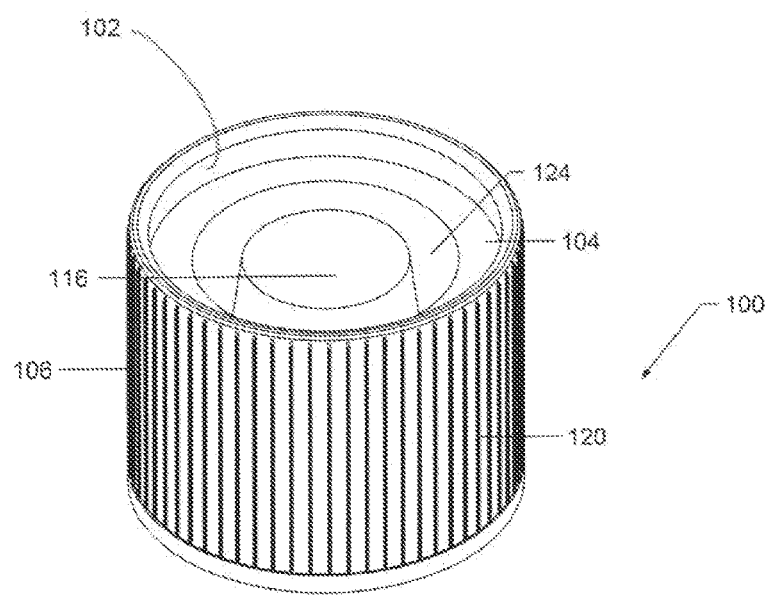
FIG. 5 is a perspective view of a first embodiment of the cap depicted in FIG. 1.

As shown in FIGS. 5, 7 and 8, in one embodiment, the cap 100 comprises a closed, top portion 102, a generally cylindrical, skirt portion 106 and an open, lower portion 122. The cap 100 is configured to removably engage with the tube 200 to form a seal, preferably an airtight or fluid tight seal, following collection of the sample into the tube 200. In a preferred embodiment, the cap 100 is configured to be screwed onto the upper portion 202 of the tube 200. The skirt portion 106 of the cap may comprise internal threads 108 that mate with complementary external threads 208 provided on the upper portion 202 of the tube 200 to removably engage the tube 200 with the cap 100 when the internal threads 108 are screwed onto the external threads 208. Preferably, the internal and external threads 108, 208 are complementary helical threads. To removably engage the cap 100 with the tube 200, the internal threads 108 can be screwed onto the external threads 208 to form a seal between the cap 100 and the tube 200, preferably an airtight or fluid tight seal. In further embodiments, the cap 100 and tube 200 may be provided with alternative engagement means for removably engaging the cap 100 with the tube 200 to form a seal.

The cap 100 further comprises first engagement means 110 extending from an underside portion 114 of the cap 100 as shown in FIG. 8, which engage with complementary second engagement means 416 extending from the upper portion 402 of the piercing insert 400. In one embodiment, the cap 100 may comprise first engagement means 110 extending from the underside 114 of the central portion 116 of the cap 100 as shown in FIGS. 6 and 8. In a preferred embodiment, the top portion 102 of the cap 100 may comprise a recessed portion 104, forming an interior, peripheral wall 124 as shown in FIG. 5. In such an embodiment, the first engagement means 110 is a projection extending from the underside 114 of the central portion 116 of the cap into the interior cavity 118 of the cap 100 and is joined to the peripheral wall 124 to form the closed, top portion 102 of the cap 100. The first engagement means 110 extending from the underside portion 114 of the cap 100 may comprise a hollow structure having a peripheral wall and one or more attachment members for joining the first engagement means 110 to the interior, peripheral wall 124. As shown in in FIG. 8, the first engagement means 110 may comprise a peripheral wall 126, which is generally cylindrical in shape and further comprise a flared lower portion 128, which is joined to the peripheral wall 124 of the cap 100.

Figure 9:
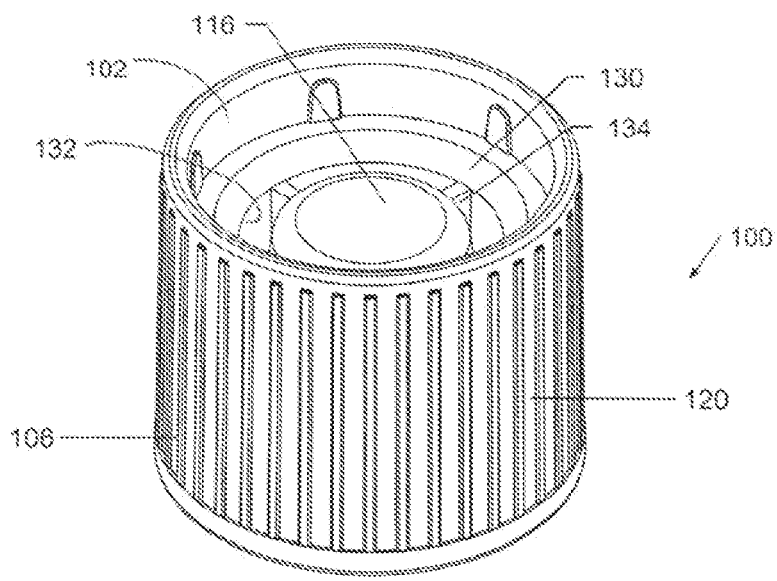
FIG. 9 is a perspective view of a second embodiment of the cap depicted in FIG. 1.
Figure 12:
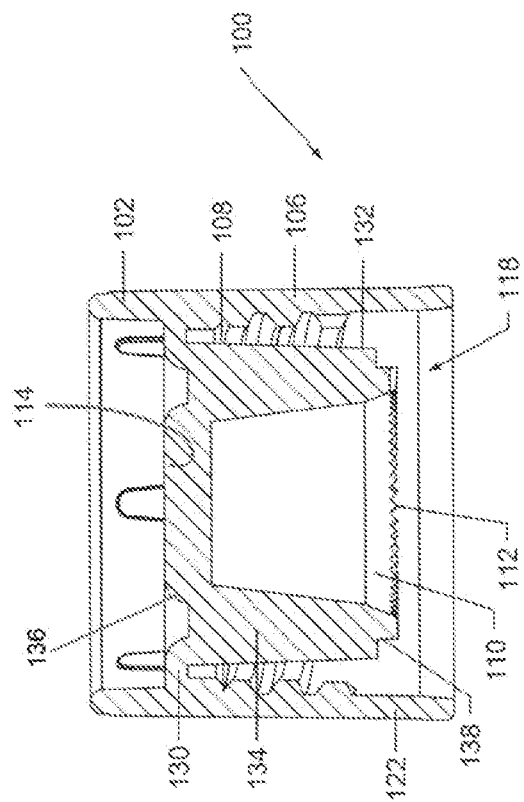
FIG. 12 is a cross-sectional view of the cap taken along line C-C in FIG. 11.
Figure 11:
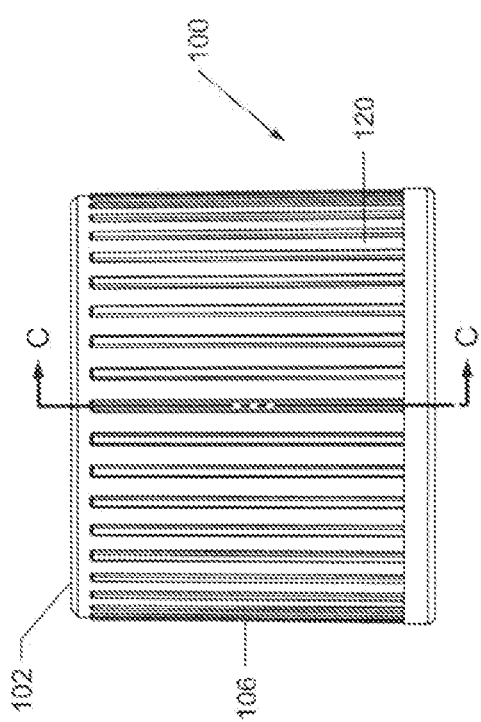
FIG. 11 is a side view of the cap depicted in FIG. 9.

FIGS. 9-12 illustrate an alternate embodiment of cap 100. As shown in FIGS. 9 and 12, the cap 100 comprises first engagement means 110 extending from the underside 114 of the central portion 116 of the cap 100. In this embodiment, to reduce the amount of materials needed to form the cap 100, while maintaining structural integrity, the first engagement means 110 may comprise a peripheral wall 136 forming a generally cylindrical structure, which is joined to an interior peripheral wall 132 of the cap 100 by one or more supporting ribs 134 and a lower portion 138 of the first engagement means 110 is further joined to the peripheral wall 132 to form the closed, top portion 102 of the cap 100. FIG. 12 shows a cross-section of the cap 100, wherein line C-C extends through supporting ribs 134. The cap 100 may further comprise recessed, annular ring 130 to provide further structural integrity.

It will be apparent to the skilled person that the first engagement means 110 may have a variety of different structures and configurations within the cap 100 so long as the first engagement means 110 is capable of engaging with the corresponding second engagement means 416 of the piercing insert 400, when the tube 200 is sealed with the cap 100, to cause the piercing insert 400 to move downward within the tube 200.

In a preferred embodiment, the first engagement means 110 may comprise plurality of engagement elements that mesh or otherwise engage with a plurality of complementary engagement elements in the second engagement means 416 of the piercing insert 400. Preferably, the first engagement means 110 may comprise a first plurality of teeth 112 as shown in FIGS. 8 and 12, which will mesh with complementary second plurality teeth 418 extending from the upper portion 402 of the piercing insert 400. As shown in FIGS. 8 and 12, the first engagement means 110 may be positioned entirely within the cavity 118 of the cap 100, and the first engagement means 110 preferably extend down from the underside portion 114 of the cap, a distance greater than 50% of the overall height of the cap 100 and even more preferably, a distance about 70% of the overall height of the cap 100. This arrangement means that the first engagement means 110 extending the underside portion 114 of the cap 100 will only interact with the complementary second engagement means 416 extending from the upper portion 402 of the piercing insert 400, when the cap 100 is completely threaded onto the tube 200 to form a seal, thereby sufficiently lowering the first engagement means 110 into the tube 200.

As will be discussed in greater detail below, in a preferred embodiment, the downward, twisting action of threading the cap 100 onto the tube 200 will result in the first engagement means 110 extending from the underside portion 114 of the cap 100 meshing or otherwise engaging with the complementary second engagement means 416 of the upper portion 402 of the piercing insert 400, thereby causing the piercing insert 400 to rotate downward within the tube 200. In further embodiments, the cap 200 and piercing insert 400 may be provided with alternative engagement means, such as complementary threads, such that the downward, twisting action of threading the cap 100 onto the tube 200 results in the corresponding downward, rotation of the piercing insert within the tube.

In further alternative embodiments, the sample collection apparatus of the present invention may comprise a cap comprising engagement means extending from an underside portion of the cap, which functions to simply push the piercing insert downward into the tube when the collection tube is capped. In such an embodiment, the cap, which may be a snap on cap or a screw cap, comprises engagement means extending from an underside portion of the cap, which when lowered into the collection tube following capping, comes into contact with an upper portion of the piercing insert, thereby forcing the piercing insert to move downward into the tube, and resulting in the disruption of the pierceable membrane and release of the reagent contained in the reagent reservoir.

In further embodiments, one or more portions of the exterior of cap 100 may be textured, such as the inclusion of annular grooves or vertical ribs, to allow the user to more easily twist or snap the cap 100 on and off the sample container, such as tube 200. FIGS. 5 and 7 and FIGS. 9 and 11 show preferred embodiments of the cap 100 comprising a plurality of raised vertical ribs 120. In still further embodiments, the cap may further comprise a sample collecting device, such as a swab or a stool collecting spoon or spatula (not shown), extending from the underside of a central portion 116 the cap 100.

As will be apparent to the skilled person, the size and shape of the cap 100 will depend on the corresponding size and shape of the sample container, such as tube 200, to be sealed. However, the dimensions of the cap 100 and the first engagement means 110 extending from the underside portion 114 of the cap 100 must be such, that when the cap 100 engages with tube 200 (for example, the cap may be threaded or snapped onto the tube 200) to seal the apparatus 10, the first engagement means 110 extending from the underside portion 114 of cap 100 is sufficiently lowered into the cavity 210 of the tube 200 to mesh or otherwise engage with the second engagement means 416 extending from the upper portion 402 of the piercing insert 400 nested within the tube 200.

The cap 100 may be made of any suitable material, which is compatible with the sample to be collected and the subsequent storage and processing of the sample. For example, for use in the collection of biological samples, the cap 100 may be comprised of a suitable plastic material, including, but not limited to: polyethylene, such as high-density polyethylene (HDPE), medium-density polyethylene (MDPE), low-density polyethylene (LDPE) and linear low-density polyethylene (LLDPE); polypropylene; polystyrene; and polycarbonate. In a more preferred embodiment, the cap 100 is made from polyethylene and can be manufactured using conventional methods, such as injection molding.

Reagent Reservoir

The sample collection apparatus of the present application further comprises a sealed, reagent reservoir contained within the sample container. The reagent reservoir may be provided as a discrete capsule or pod containing the desired reagent, which is inserted into the sample container. Alternatively, the reagent reservoir can be formed within the sample container itself. The capacity of the reagent reservoir and the choice of reagent stored within the reservoir will be determined by the needs and preferences of the user.

In one embodiment, the reagent reservoir 300 containing the desired reagent, and more preferably a preservative reagent when the sample to be collected is a biological sample, may be in the form of a discrete capsule or pod containing a predetermined amount of the desired reagent. The size and shape of the reagent reservoir 300 will depend on the desired quantity of the desired reagent and the corresponding shape and size of the sample container, such as tube 200, which will contain the reagent reservoir 300 and the collected sample.

As shown in FIGS. 13A, 13B, 14 and 15, the reagent reservoir 300 may be in the form of a capsule, which is generally cylindrical in shape and comprises a cavity 314 for containing the desired reagent 316. The body 302 of the reagent reservoir 300 comprises an upper portion 304 defining an opening 306, which is covered by the pierceable membrane 312 in the form of a suitable plastic and/or metallic foil film. The reagent reservoir 300 further comprises a closed, lower portion 318, which may have a round or conical bottom 320 (or any other shaped bottom) that corresponds to the shape of the bottom 212 of the tube 200.

Figure 13B:
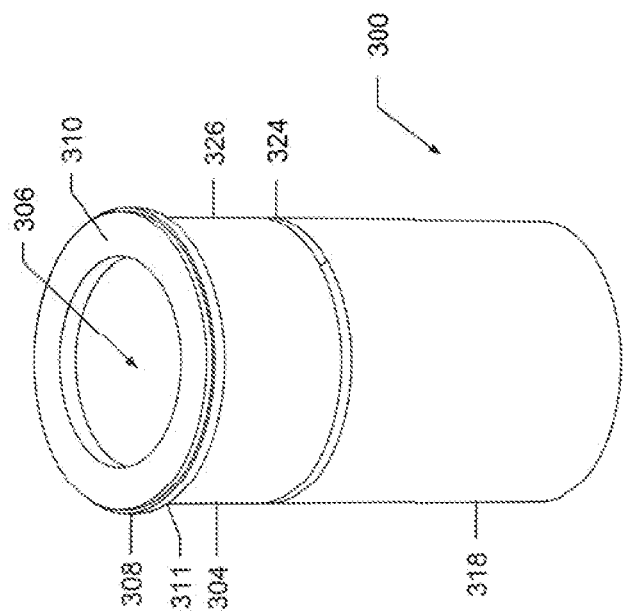
FIG. 13B is a perspective view of the reagent reservoir of FIG. 13A, without the pierceable membrane.
Figure 13A:
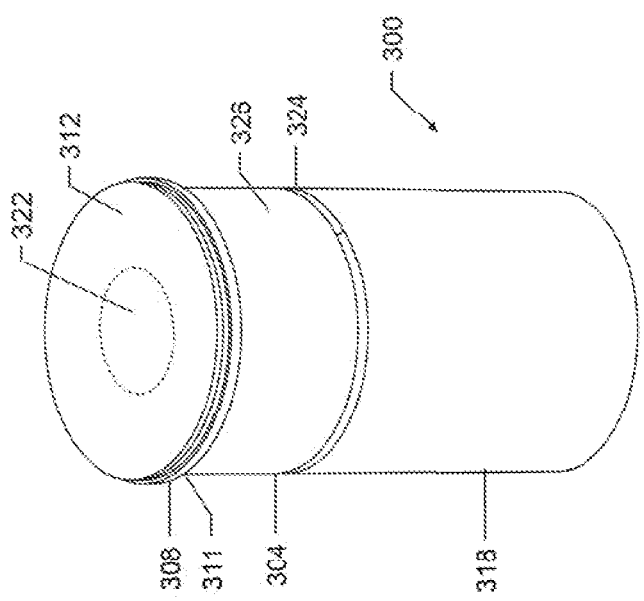
FIG. 13A is a perspective view of the reagent reservoir depicted in FIG. 1.

FIG. 13B shows the reagent reservoir 300 without the pierceable membrane 312. To facilitate attachment of the pierceable membrane 312 over the opening 306 of the reagent reservoir 300, the upper portion 304 may comprise a sealing surface in the form of a flange 310 extending inwardly from peripheral edge 311 of the upper portion 304 of the reagent reservoir 300. Following the filling of the cavity 314 with the predetermined amount of the desired reagent 316 (not shown), the pierceable membrane 312 can be attached to the body 302 of the reagent reservoir 300, using any suitable method, such as heat sealing. In one embodiment, the pierceable membrane 312 may be attached by laying the pierceable membrane 312 over the sealing surface formed by flange 310 and applying heat. Alternatively, the pierceable membrane 312 may be attached to the sealing surface formed by flange 310 using an adhesive, ultrasonic welding or any other suitable method, such that a fluid tight seal is formed over the opening 306.

The reagent reservoir 300 may further comprise a skirt portion 308, which extends along a peripheral edge 311 of the reagent reservoir 300 and an annular groove 324 defined in the exterior surface 326 of the upper portion 304 of the reagent reservoir. When the reagent reservoir 300 is seated in the lower portion 204 of the tube 200, the skirt portion 308 will frictionally engage with first retaining lip 222 of the tube 200 and the second retaining lip 224 of the tube 200 is retained within the annular groove 324, allowing the reagent reservoir 300 to fit snuggly within the lower portion 204 of the tube 200, thereby ensuring that the reagent reservoir 300 is not dislodged during transport, even if the tube 200 is turned upside down.

Alternatively, in a further embodiment, the reagent reservoir can be formed directly in the sample container, for example, in the lower portion 204 of the collection tube 200 (not shown) by adding a pre-determined quantity of the desired reagent, and more preferably a preservative reagent, into the tube 200 and covering the desired reagent with a pierceable membrane in the form of a suitable plastic and/or metallic foil film. The pierceable membrane is preferably configured to cover the opening of the reservoir, with the excess plastic or foil film forming a skirt or flange, which abuts the interior surface of the tube 200 when the pierceable membrane is seated within the tube 200. Preferably, heat-sealing is used to attach the plastic or foil film to the interior surface of the tube 200, thereby sealing the desired reagent within the reagent reservoir. Alternatively, the pierceable membrane 312 may be attached to the interior surface of the tube 200 using an adhesive, ultrasonic welding or any other suitable method, such that a fluid tight seal is formed over the opening of the reagent reservoir.

Regardless of whether the reagent reservoir is provided as a separate capsule (or other discrete unit, such as a pod) or is formed directly within the collection tube, the choice of materials and manufacturing materials should be selected to provide a fluid-tight reservoir over a wide range of temperatures and atmospheric pressures, which can result from long-term storage and transportation of the containing apparatus, including air transport.

In embodiments, wherein the reagent reservoir 300 is provided in the form of a capsule or a pod, the body 302 of reagent reservoir 300 may be formed using any suitable plastic or metallic material, which is compatible with the sample to be collected and the subsequent storage and processing of the sample. For example, for the collection of biological samples, preferably, the body 302 of the reagent reservoir 300 may be formed using a suitable plastic material, including, but not limited to: polyethylene, such as high-density polyethylene (HDPE), medium-density polyethylene (MDPE), low-density polyethylene (LDPE) and linear low-density polyethylene (LLDPE); polypropylene; polystyrene; and polycarbonate. Alternatively, the reagent reservoir 300 may be formed from a suitable metallic material, such as aluminum foil. In a more preferred embodiment, the body 302 of the reagent reservoir 300 is made from polypropylene and can be manufactured using conventional methods, such as injection molding. Preferably, the pierceable membrane is formed from a plastic, including, but not limited to: polyethylene, such as high-density polyethylene (HDPE), medium-density polyethylene (MDPE), low-density polyethylene (LDPE) and linear low-density polyethylene (LLDPE); and polypropylene. The pierceable membrane may also be formed from a metallic foil or combination of metallic and plastic materials.

Piercing Insert

The sample collection apparatus of the present invention further comprises a piercing insert comprising one or more piercing elements. The piercing insert is nested within the sample container, such that the one or more piercing elements are located above the pierceable membrane or film of the reagent reservoir. Following collection of a sample into the sample container, the action of sealing the sample container with the cap causes the piercing insert to move downwards within the sample container, whereby the one or more piercing elements disrupt the pierceable membrane or film of the reagent reservoir.

As shown in FIGS. 16 to 21, in one embodiment, the piercing insert 400 may be generally cylindrical in shape and is intended to nest within the cavity 210 of the generally cylindrical tube 200 shown in FIGS. 1 to 4. It will be appreciated that the size and shape of the piercing insert 400 will depend on the corresponding size and shape of the sample container, such as tube 200, in which the piercing insert 400 will be received.

The piercing insert 400 is open at both ends to allow the biological sample collected into the opening 206 of the tube 200 to flow through the piercing insert 400 and to combine with the desired reagent, and more preferably a preservative reagent 316 when the sample to be collected is a biological sample, once the pierceable membrane 312 of the reagent reservoir 300 has been disrupted. The piercing insert 400 may be formed as a generally cylindrical sleeve, preferably having a tapered portion 407 and a reduced diameter, lower portion 408.

As shown in FIGS. 16 to 18, in one embodiment, the piercing insert 400 comprises an upper portion 402 defining an upper opening 406. The upper portion 402 comprises an upper peripheral edge 404. The upper portion 402 comprises second engagement means 416 extending therefrom, which are complementary to the first engagement means 110 extending from the underside portion 114 and disposed within cavity 118 of the cap 100. As shown in FIGS. 16 and 18, the second engagement means 416 may be provided such that the second engagement means 416 are recessed below the upper peripheral edge 404.

Figure 21:
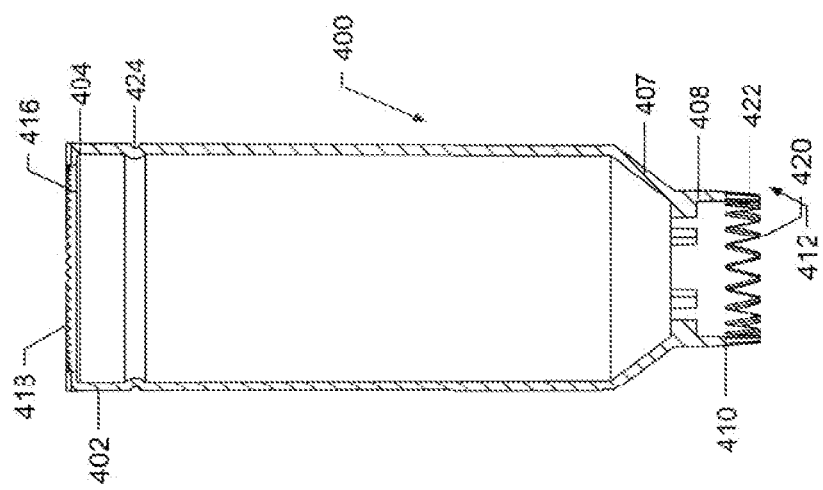
FIG. 21 is a cross-sectional view of the insert taken along line F-F in FIG. 17.
Figure 20:
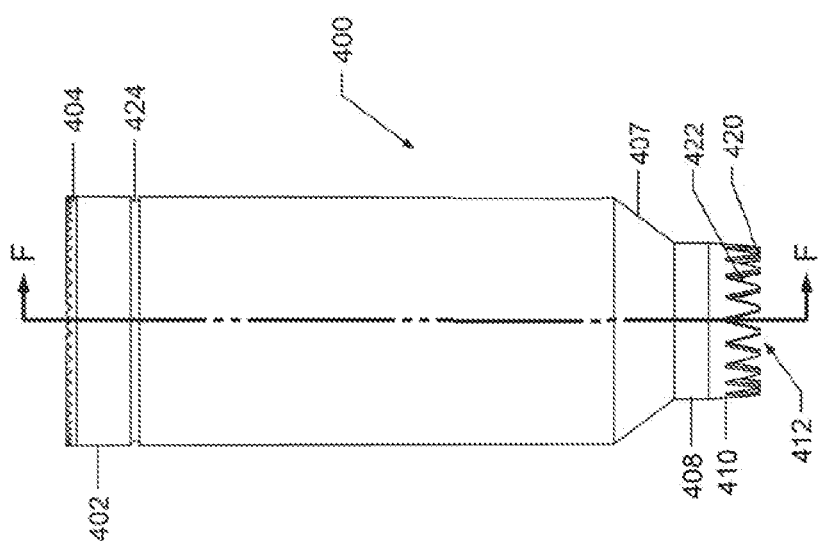
FIG. 20 is a side view of the insert depicted in FIG. 19.
Figure 19:
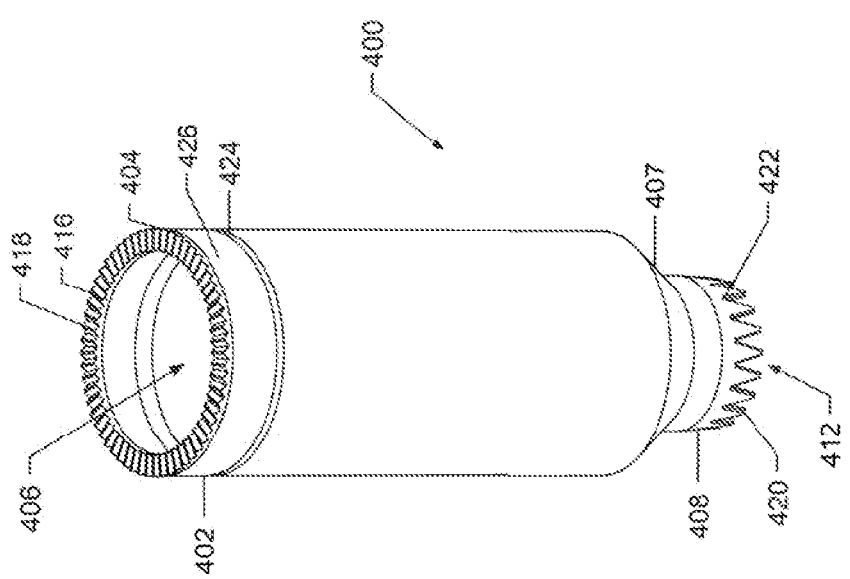
FIG. 19 is a perspective view of a second embodiment of the insert depicted in FIG. 1.
Figure 22:
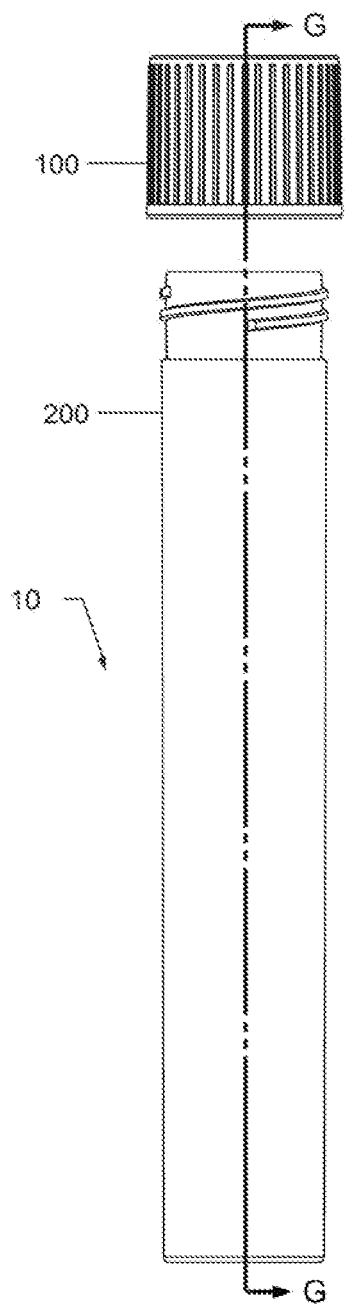
FIG. 22 is side view of the apparatus depicted in FIG. 1, showing the cap separated from the collection tube.

In another embodiment, as shown in FIGS. 19 to 21, the piercing insert 400 comprises second engagement means 416 extending from the upper peripheral edge 404, which are complementary to the first engagement means 110 extending from the underside portion 114 and disposed within cavity 118 of the cap 100.

It will be apparent to the skilled person that the second engagement means 416 extending from the piercing insert 400 may have a variety of different structures and configurations so long as the second engagement means 416 is capable of engaging with the corresponding first engagement means 110 of the cap 100, when the sample container, such as tube 200, is sealed with the cap 100, to cause the piercing insert 400 to move downward within the sample container.

In a preferred embodiment, the piercing insert 400 comprises second engagement means 416, which may comprise plurality of engagement elements that mesh or otherwise engage with a plurality of complementary engagement elements in the first engagement means 110 of the cap 100. In one embodiment, the second engagement means 416 extending from the upper portion 402 of the piercing insert 400 as shown in FIGS. 16 to 18 or extending from the upper peripheral edge 404 of the piercing insert 400 as shown in FIGS. 19 to 21, may be in the form of a second plurality of teeth 418, which are capable of meshing with a complementary first plurality of teeth 112 extending from the underside portion 114 of the cap 100, when the cap 100 is threaded onto the tube 200. In further embodiments, the cap 100 and piercing insert 400 may be provided with alternative engagement elements, such as complementary threads, such that the downward, twisting action of threading the cap 100 onto the tube 200 results in the corresponding downward movement, and more preferably downward rotation, of the piercing insert within the tube as discussed in greater detail below.

In alternate embodiments, it is sufficient that the action of snapping or twisting the cap onto the collection tube (or any other suitable sample container) results in the piercing insert being moved downward within the tube. In such embodiments, the sample collection apparatus of the present invention may comprise a cap comprising engagement means extending from an underside portion of the cap, which functions to simply push the piercing insert downward into the tube when the collection tube is capped.

The piercing insert 400 further comprises a lower portion 408 defining a lower opening 412. In a preferred embodiment, as shown in FIGS. 16 to 21, the piercing insert 400 may comprise a tapered portion 407 and a lower portion 408 extending therefrom. The lower portion 408 has a reduced diameter compared to the upper portion 402 of the piercing insert 400.

Figure 23:
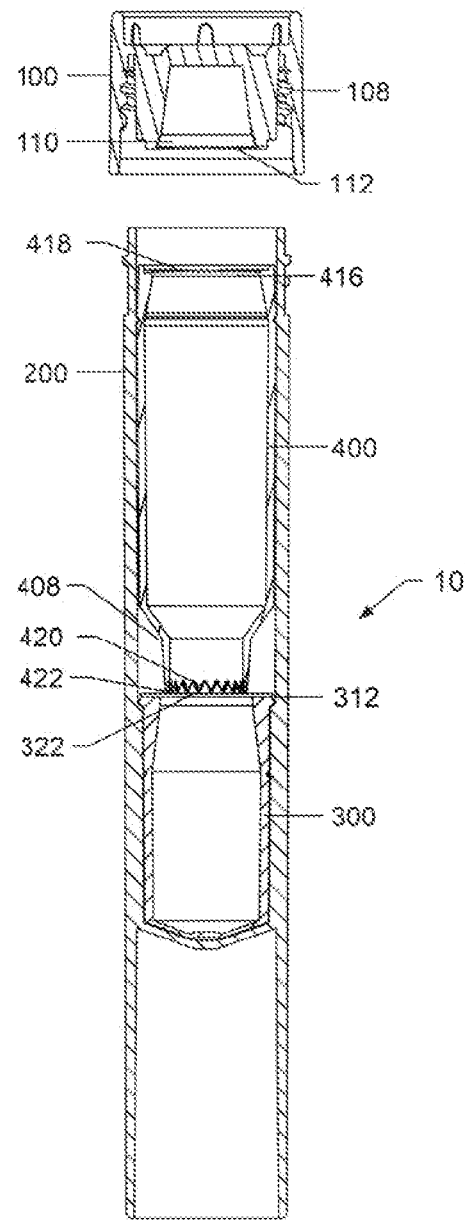
FIG. 23 is a cross-sectional view of the apparatus taken along line G-G in FIG. 22, showing the insert and reagent reservoir nested within the collection tube and the insert being in a first position (non-piercing position) within the collection tube.
Figure 24:
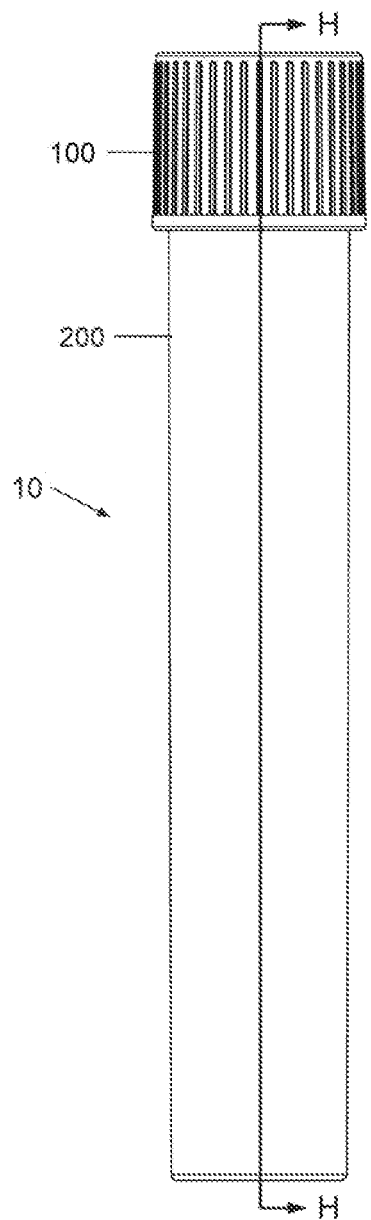
FIG. 24 is a side view of the apparatus depicted in FIG. 1, showing the cap threaded onto the collection tube to form a seal.
Figure 25:
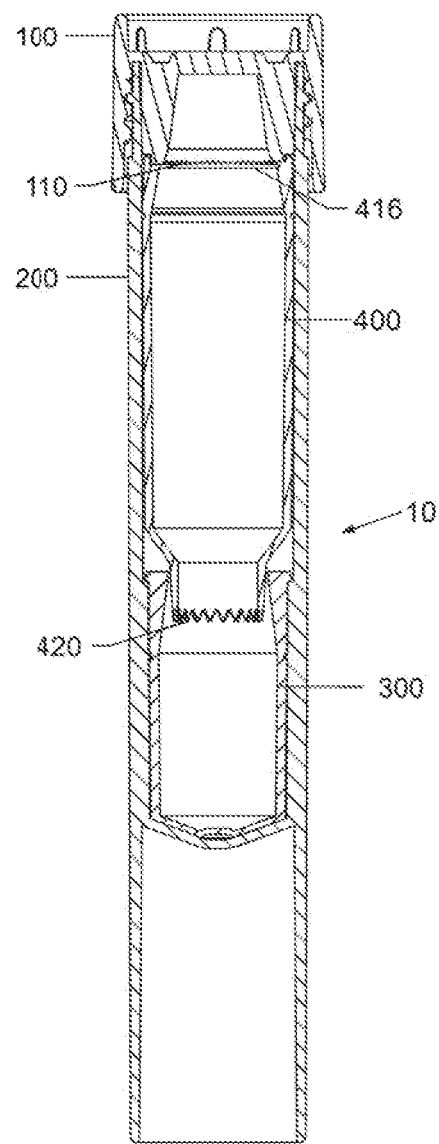
FIG. 25 is a cross-sectional view of the apparatus taken along line H-H in FIG. 24, showing the insert and reagent reservoir nested within the collection tube and the insert being in a second position (piercing position) within the collection tube.

In a preferred embodiment, the lower portion 408 comprises a lower peripheral edge 410. One or more piercing elements 420 extend from the lower peripheral edge 410. Preferably, the one or more piercing elements 420 are formed integrally with the lower peripheral edge 410, such that the piercing insert 400 can be formed as a single piece. In one embodiment, the lower peripheral edge 410 may comprise a single piercing element, such as a sharpened point or tooth extending from the lower peripheral edge 410. In a more preferred embodiment, the lower peripheral edge 410 comprises a plurality of sharpened points or teeth to form a serrated edge 422 as shown in FIGS. 16 to 21. In a preferred embodiment, the lower portion 408 is sized and configured to be received in the sealed opening 322 of the reagent reservoir 300 following disruption of the pierceable membrane 312. As shown in FIGS. 23 and 25, in a preferred embodiment the diameter of the lower portion 408 comprising the serrated edge 422 is marginally smaller than the diameter of the sealed opening 322 of the reagent reservoir 300 to facilitate removal of substantially the entire pierceable membrane 312 from the reagent reservoir 300 when tube 200 is sealed with the cap 100.

While the overall dimensions of the piercing insert 400 will vary depending on the corresponding dimensions of the tube 200 (or any other suitable sample container), which will receive the piercing insert 400, it will be appreciated that the length of the piercing insert 400 must be shorter than the length of the tube 100, such that when the piercing insert 400 is nested within the cavity 210 of the tube 200, the piercing insert 400 is received entirely within the cavity 210 of the tube 200 and the one or more piercing elements 420 are positioned above the pierceable membrane 312 of the reagent reservoir 300. In a preferred embodiment, to prevent the piercing insert 400 from accidently falling out of the tube 200 during use and to prevent premature movement of the piercing insert 400 within the tube 200 prior to capping the tube 200, the widest portion of the piercing insert 400 is sized to have an outer diameter that allows the piercing insert 400 to be snuggly nested within the cavity 210 of the tube 200 and also allows subsequent movement of piercing insert 400 within the tube 200 following the capping of the tube 200 as discussed in greater detail below. Moreover, the piercing insert 400 can be provided with an annular groove 424 defined in the exterior surface 426 of the upper portion 402 of the piercing insert 400 as shown in FIGS. 16 to 21. When the piercing insert 400 is nested within the tube 200, the retaining lip 226 of the tube 200 is retained within the annular groove 424 to prevent premature movement of the piercing insert 400 within the tube 200 prior to capping the tube 200.

Preferably, the piercing insert is further sized such that when the piercing insert is nested within the cavity 210 of the tube 200 and positioned above the pierceable membrane 312 of the reagent reservoir 300, the piercing insert is also seated below the opening 206 of the tube 200, preferably about 2 to about 3 mm below the opening 206 of the tube 200. Such an arrangement is advantageous as it reduces the risk that the piercing insert 400 prematurely disrupts the pierceable membrane 312 of the reagent reservoir 300 prior to the capping of the tube 200.

The piercing insert 400 is movable from a first position (e.g. non-piercing position) to a second position (e.g. piercing position) within the tube 200 (or any other suitable sample container), preferably in response to the downward, twisting action of threading the cap 100 onto the tube 200. For example, as shown in FIG. 23, when the cap 100 is separated from the tube 200 and the piercing insert 400 is in the first position (e.g. non-piercing position), the one or more piercing elements 420 are located above the pierceable membrane 312. Following the collection of the sample, preferably a biological sample, into the tube 200, the cap 100 is removably engaged with the tube 200, preferably by threading the cap 100 onto the tube 200. In a preferred embodiment, the downward, twisting action of threading the cap 100 onto the tube 200 causes the first engagement means 110 extending from the underside portion 114 of the cap 100 to be lowered into the cavity 210 of the tube 200 and to mesh or otherwise engage with the complementary second engagement means 416 extending from the upper portion 402 (or the upper peripheral edge 404) of the piercing insert 400, this in turn causes the piercing insert 400 to also rotate and move downward within the tube 400 from the first position to the second position. As shown in FIG. 25, the twisting action of threading the cap 100 onto the tube 200 causes the piercing insert 400 to rotate and move downward within the tube 200 to the second position (e.g. piercing position), such that the one or more piercing elements 420 are brought into contact with and disrupt the pierceable membrane 312, thereby allowing fluid communication between the cavity 210 of the tube and the reagent reservoir 300.

In contrast to conventional sample collection systems comprising a sealed reservoir containing a reagent and a stationary piercing element, which merely punctures the sealed reservoir (e.g. pierces a single puncture hole) to release the reagent, in preferred embodiments of the apparatus 10 of the present invention, the piercing insert 400 is capable of removing a substantial portion of the pierceable membrane 312 covering the reagent reservoir 300. By preferably rotating the piercing insert 400, the one or more piercing elements 320 are capable of disrupting a larger area of the pierceable membrane 312 as compared to the prior art stationary piercing elements. By disrupting a larger area of the pierceable membrane, and more preferably cutting away a substantial portion of the top of the sealed reagent reservoir 300, this ensures maximum release of the entire volume of the desired regent 316, and more preferably a preservation reagent, contained therein.

The piercing insert 400 may be made of any suitable material, which is compatible with the sample to be collected and the subsequent storage and processing of the sample. For example, for the collection of biological samples, preferably, the piercing insert 400 may be of a suitable plastic material, including, but not limited to: polyethylene, such as high-density polyethylene (HDPE, medium-density polyethylene (MDPE), low-density polyethylene (LDPE) and linear low-density polyethylene (LLDPE); polypropylene; polystyrene; and polycarbonate. In a more preferred embodiment, the piercing insert 400 is made from polypropylene and can be manufactured using conventional methods, such as injection molding.

Funnel

As shown in FIGS. 26 to 31, in one embodiment, the apparatus 10 may further comprise a removable funnel 500. The funnel 500 comprises an upper portion 502 defining an upper opening 504 for receiving a sample, a tapered portion 506 and a reduced diameter, lower portion 508 defining a lower opening 510. The interior of the funnel 500 comprises an interior channel 512 extending from the upper opening 502 to the lower opening 510 through which the received sample is directed into the cavity 210 of the tube 200.

Figure 28:
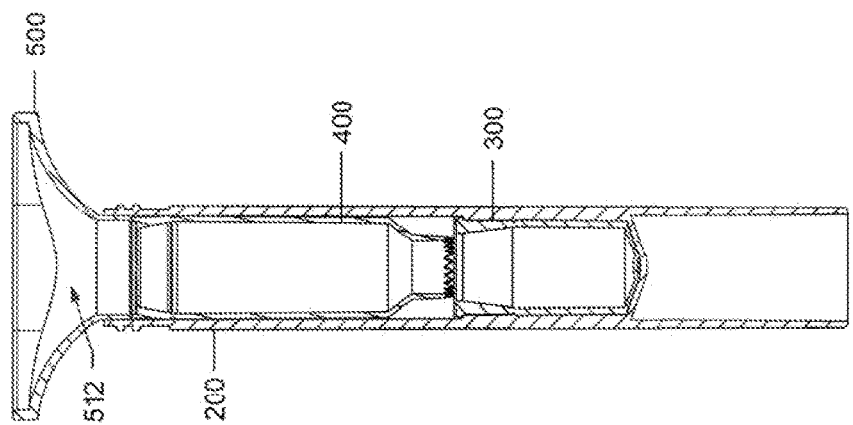
FIG. 28 is a cross-sectional view of the view of the funnel and the collection tube taken along line I-I in FIG. 26, showing the insert and reagent reservoir nested within the collection tube.
Figure 27:
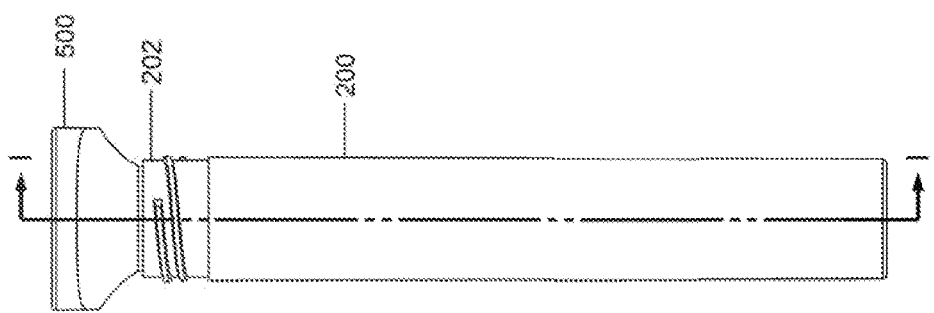
FIG. 27 is a side view of the funnel of FIG. 26, showing the funnel inserted into the upper portion of the collection tube depicted in FIG. 1.
Figure 26:
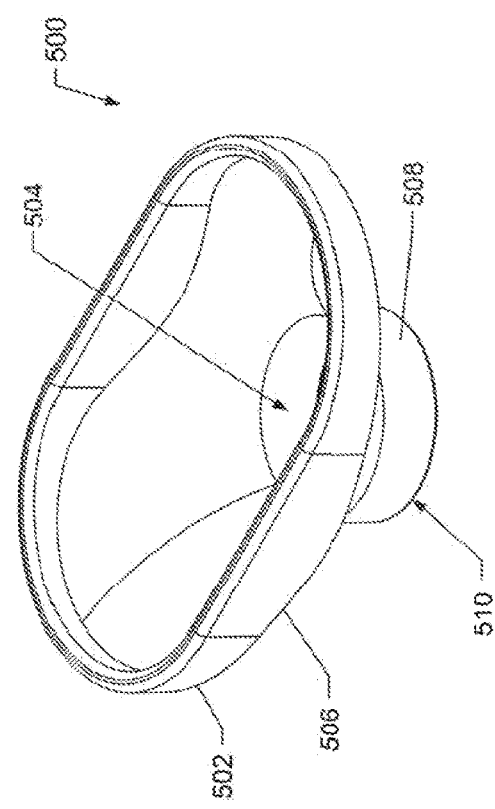
FIG. 26 is a perspective view of a first embodiment of a funnel for use with the apparatus depicted in FIG. 1.
Figure 31:
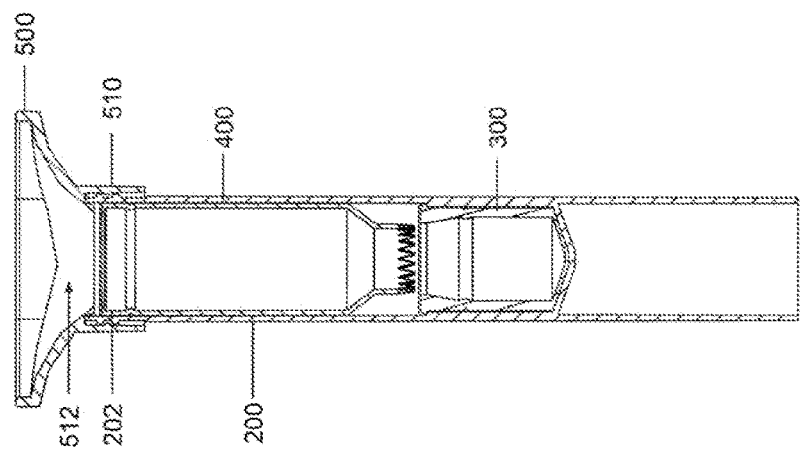
FIG. 31 is a cross-sectional view of the view of the funnel and the collection tube taken along line J-J in FIG. 30, showing the insert and reagent reservoir nested within the collection tube.
Figure 30:
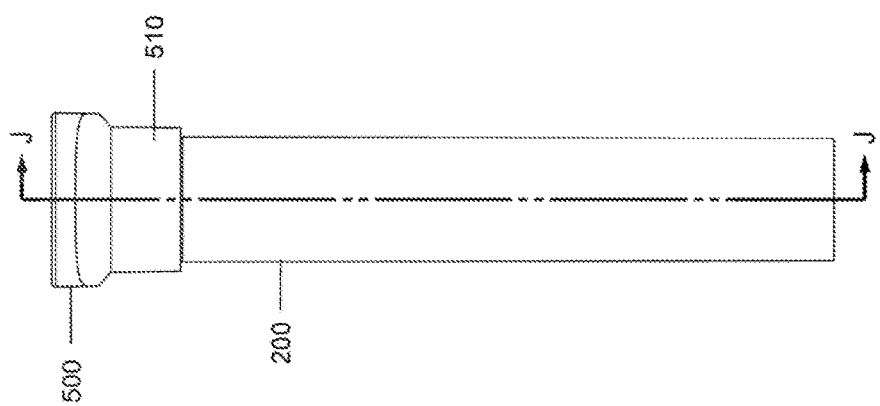
FIG. 30 is a side view of the funnel of FIG. 29, showing the funnel attached to the upper portion of the collection tube depicted in FIG. 1.
Figure 29:
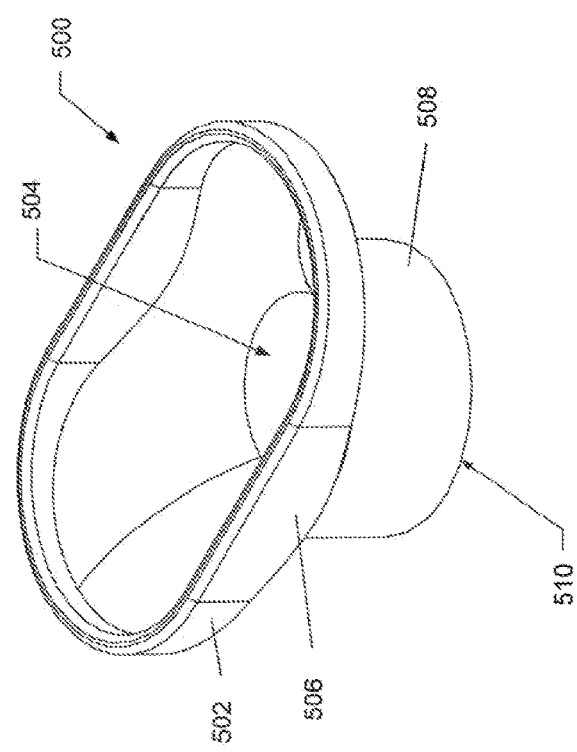
FIG. 29 is a perspective view of a second embodiment of a funnel for use with the apparatus depicted in FIG. 1.

It will be appreciated that the size and shape of the funnel 500 will depend on the corresponding size and shape of the sample container, such as tube 200, with which the funnel 500 will be used and the type and volume of sample to be collected. In one embodiment, as shown in FIGS. 26 to 28, the funnel 500 is sized and configured so that lower portion 510 of the funnel 500 can be inserted into the upper portion 202 of the tube 200 by the user prior to collecting the sample. In another embodiment, as shown in FIGS. 29 to 31, the funnel 500 is sized and configured so that lower portion 510 of the funnel 500 can be placed over the upper portion 202 of the tube 200 by the user prior to collecting the sample. Preferably, the funnel is made from a flexible material, and the lower portion 508 of the funnel 500 is configured to frictionally engage with the upper portion 202 of the tube, allowing the user to snap the funnel 500 onto the tube 200.

In another embodiment, the lower portion 508 of the funnel 500 may be provided with internal threads (not shown) complementary to the external threads 208 on the upper portion 202 of the tube 200 to allow the funnel 500 to be removably engageable with the tube 200. The funnel 500 can be secured onto the tube 200 by screwing the internal threads of the funnel 500 onto the external threads 208 of the tube 200 prior to collecting the sample. After collection of the sample, the funnel 500 can be removed and replaced with the cap 100 to seal the apparatus 10.

The funnel 500 may be made of any suitable material, which is compatible with the sample to be collected and the subsequent storage and processing of the sample. For example, for use in the collection of biological samples, preferably, the funnel 500 may be of a suitable plastic material, including, but not limited to: polyethylene, such as high-density polyethylene (HDPE), medium-density polyethylene (MDPE), low-density polyethylene (LDPE) and linear low-density polyethylene (LLDPE); polypropylene; polystyrene; and polycarbonate. In embodiments where a flexible funnel is desired, the funnel 500 may be made from suitable thermoplastic elastomers (TPEs), also known as thermoplastic rubbers. In a more preferred embodiment, the funnel is made from rubber and polystyrene. The funnel 500 can be manufactured using conventional methods, such as injection molding.

Method for Collecting and Combining a Sample with a Reagent

In a further aspect, provided is a method for collecting a sample, preferably a biological sample, and combining the sample with a desired reagent, preferably a preservative reagent, using the sample collection apparatus of the present invention.

In one embodiment, the method comprises: providing a sample collection apparatus 10 as described above; adding the sample, preferably a biological sample, into the tube 200 (or any other suitable sample container); and closing the apparatus 10 by removably engaging the cap 100 with the tube 200; whereby the piercing insert 400 is moved downward, and more preferably, rotated downward, within the tube 200 from the first position (e.g. non-piercing position) to the second position (e.g. piercing position), disrupting the pierceable membrane 312 to expose the sample, preferably a biological sample, to the desired reagent 316, preferably a preservative reagent. In a preferred embodiment, the pierceable membrane 312 of the reagent reservoir 300 is substantially removed by the one or more piercing elements 420 of the piercing insert 400.

The size and shape of the sample collection apparatus can be configured to facilitate the collection and storage of the desired sample, which is preferably a biological sample. The biological sample collected may include biological samples in both substantially liquid (including suspensions and gels) and solid form. The biological sample may be obtained from cell cultures, plants and animals. In a preferred embodiment, the biological sample is obtained from a human subject and may include a variety of bodily fluids and tissues.

Non-limiting examples of liquid biological samples obtained from a human subject, include, but are not limited to: blood, plasma, serum, urine, liquid fecal matter, tears, sweat, saliva, breast milk, amniotic fluid, seminal fluid, cerebral spinal fluid, or colostrum sample. In a preferred embodiment, the methods of the present invention can be used to collect and preserve a liquid biological sample, the liquid biological sample being a saliva sample from a human subject.

Non-limiting examples of solid biological samples obtained from a human subject, include, but are not limited to: hair, solid fecal matter (e.g. stools), and tissue obtained from skin, muscle, organs and/or the nervous system. In a preferred embodiment, the methods of the present invention can be used to collect and preserve a solid biological sample, the solid biological sample being a stool sample from a human subject.

It will be apparent to the skilled person that the sample collection apparatus and method of use of the present invention may be used to collect a variety of different types of samples including, but not limited to: food and beverage samples (including fresh and processed food products), environmental samples (including water, soil, minerals, liquid and solid wastes), and chemical samples (including polymers, fertilizers, colourants, lubricants, and other industrial chemicals).

It will also be apparent that the choice and amount of the desired reagent used will depend on the type and amount of sample collected and the intended storage, shipping and subsequent processing of the collected sample. In the case of biological samples, the collection apparatus may preferably be provided with a preservative reagent. The skilled person may employ a suitable preservative agent as known in the art. Other reagents which may be appropriate for use with biological samples include, but are not limited, to cell culture media, viral transport media, saline and buffers.

In a preferred embodiment, provided is a method for collecting and preserving a saliva sample. The sample collection apparatus 10 can be provided with a reagent reservoir 300 filled with an appropriate amount of any suitable nucleic acid preservative reagent, as known in the art. The nucleic acid preservative reagent may be a DNA preservative reagent and/or an RNA preservative reagent. A funnel 500 as described above, can be used to facilitate the sample collection. In one embodiment, the lower portion 508 of the funnel 500 can be simply snapped onto the upper portion 202 of the tube 200 or any other suitable sample container. Alternatively, if the lower portion 508 of the funnel 500 is configured with internal threads, the funnel 500 can be screwed onto external threads 208 provided on the upper portion 202 of the tube 200 or any other suitable sample container. Preferably, the sample container is tube 200 and the exterior of the tube 200 comprises a fill-line indicia to ensure that the user collects the correct amount of the saliva sample. The user can repeatedly spit directly into the funnel 500 until the requisite amount of saliva is collected within the tube 200. The funnel 500 can then be removed from the tube 200 and the user can seal the apparatus for storage, shipping and/or further processing of the biological sample by preferably threading the cap 100 onto the tube 200. In such embodiments, the action of twisting the cap 100 onto the tube 100 will cause the piercing insert 400 to rotate downward within the tube 200, disrupting the pierceable membrane 312 and releasing the nucleic acid preservative reagent to combine with the collected saliva sample.

In a further preferred embodiment, provided is a method for collecting and preserving a stool sample. The sample collection apparatus 10 will be provided with a reagent reservoir filled with an appropriate amount of any suitable nucleic acid preservative reagent, as known in the art. Using a spoon or a spatula, which may optionally be provided attached to the underside of the central portion 116 of the cap 100, the user can collect and transfer the required amount of the stool sample into the tube 200 or any other suitable sample container. As described above, following collection of the stool sample, the apparatus 10 can be sealed by preferably threading the cap 100 onto the tube 200, wherein the action of twisting the cap 100 onto the tube 200 will also cause the release of the nucleic acid preservative reagent from the reagent reservoir 300 to combine with the collected stool sample.

Kit for Collecting and Combining a Sample with a Reagent

In a further aspect, provided is a kit comprising the sample collection apparatus of the present invention and instructions for sealing the apparatus and releasing the reagent, following the collection of the sample. Preferably, the kit is for use in the collection of a biological sample and combining the collected biological sample with a preservative reagent.

The apparatus 10 may be provided in an unassembled form, requiring the user to insert the reagent reservoir 300 and piercing insert 400, and optionally, a funnel 500 into the tube 200 (or any other suitable sample container) prior to use. Preferably, the apparatus 10 may be provided in a partially assembled form, wherein the apparatus 10 is provided with the reagent reservoir 300 and piercing insert 400 already inserted into the tube 200.

It will be appreciated that the sample collection apparatus 10 will be provided with either the cap 100 preferably separated from the tube 200 (or any other suitable sample container) or alternatively with the cap 100 only partially screwed onto the tube 200 (or any other suitable sample container), such that the first engagement means 110 in the cap 100 and the complementary second engagement means 416 in the piercing insert 400 remain separated, to ensure that the reagent reservoir 300 remains intact until the user has collected the sample, preferably a biological sample, and intends to seal the apparatus 10 for storage, shipping and/or further processing of the sample. In embodiments where the apparatus 10 is provided with a funnel 500, the apparatus 10 can be provided with the cap 100 separated from the tube 100 and the funnel 500 already attached onto the sample container (for example, the upper portion 202 of the tube to streamline the collection process by the user.

The kit may further comprise a suitable container for providing the apparatus 10 to the end user. The container may optionally include a support, such as a foam support or a plastic tray, comprising cavities defined therein to receive and retain the components of the apparatus 10, the components being provided as discrete parts or partially assembled together. Preferably the container is a conventional plastic clamshell container having appropriately sized recesses defined therein for containing the components of the apparatus 10. The container may also be used to ship or transport the sealed apparatus 10 following the collection of the sample, which is preferably a biological sample. Preferably, the container is sized and configured to be suitable for a variety of land and air shipping and transport methods.

The kit comprises instructions for sealing the apparatus 10 and releasing the reagent 316, preferably a preservative reagent, following the collection of the sample, preferably a biological sample, and which direct the user to seal the apparatus 10 by screwing the cap 100 onto the tube 200, the action of which will result in the piercing insert 400 disrupting the pierceable membrane 312 and releasing the reagent 316. The instructions may further instruct the user how to collect the sample, which is preferably a biological sample, into the tube 200, including the relevant amount of sample to be collected, and instructions for shipping the collected sample. The instructions may be provided as written instructions provided as an insert and/or as printed on the packaging containing the apparatus 10.

In one embodiment, provided is a kit for collecting and preserving a saliva sample comprising the sample collection apparatus 10 of the present invention, the apparatus containing a preservative reagent, which is preferably a DNA preservative reagent and/or an RNA preservative reagent, and instructions for sealing the apparatus 10 and releasing the preservative reagent 316, following the collection of the saliva sample. The apparatus 10 is provided with the reagent reservoir 300 prefilled with any suitable nucleic acid preservative reagent, as known in the art. The apparatus 10 is also provided with a funnel 500 to assist the user in collecting the saliva into the sample container, such as tube 200. Preferably, the sample container is tube 200 and the exterior of the tube 200 comprises a fill-line indicia to ensure that the user collects the correct amount of the saliva sample. The kit may optionally, further comprise a shipping container, which may be in the form a suitably sized box or envelope, and which can be used to ship or transport the sealed apparatus 10 following the collection of the saliva sample.

In a further embodiment, provided is a kit for collecting and preserving a stool sample comprising the sample collection apparatus 10 of the present invention, the apparatus containing a preservative reagent, which is preferably a DNA preservative reagent and/or an RNA preservative reagent, and instructions for sealing the apparatus 10 and releasing the preservative reagent 316, following the collection of the stool sample. The apparatus 10 is provided with the reagent reservoir prefilled with any suitable nucleic acid preservative reagent, as known in the art. The apparatus 10 is also provided with a sample collection device, such as a spoon or a spatula to assist the user in collecting the stool sample and transferring the stool sample into the sample container, such as tube 200. The kit may optionally, further comprise a shipping container, which may be in the form a suitably sized box or envelope, and which can be used to ship or transport the sealed apparatus 10 following the collection of the stool sample.

Although the invention has been described with reference to illustrative embodiments, it is to be understood that the invention is not limited to these precise embodiments, and that various changes and modification are to be intended to be encompassed in the appended claims.

REFERENCES

Galior, Kornelia D. and Baumann, Nikola A. (2020) Challenges with At-home and Mail-in Direct-to-Consumer Testing. Clinics in Laboratory Medicine, 40 (1), 25-36.

Salivanti, Francesa; Gelmini, Stefania; Constanza, Filomena; Mancini, Irene; Sonnati, Gemma; Simi, Lisa; Pazzagli, Mario; and Pinzani, Pamela. (2020) The preanalytical phase of the liquid biopsy. New Biotechnology, 55, 19-29.

Langie, S. A. S.; Szarc Vel Szic, K.; Declerck, K.; Traen, S.; Koppen, G.; Van Camp, G.; Schoeters, G.; Vanden Berghe, W.; De Boever, P. (2016) Whole-genome saliva and blood DNA methylation profiling in individuals with a respiratory allergy. PLoS ONE 11(3): e0151109.

Maria, N. I.; Brkic, Z.; Waris, M.; van Helden-Meeuwsen, C. G.; Heezen, K.; van de Merwe, J. P.; van Daele, P. L.; Dalm, V. A. S. H.; Drexhage, H. A.; Versnel, M. A. (2014). MxA as a clinically applicable biomarker for identifying systemic interferon type I in primary Sjogren's syndrome. Ann. Rheum. Dis., 73, 1052-1059

The invention claimed is:

1. An apparatus for collecting and combining a sample with a reagent, the apparatus comprising:
   a container comprising an upper portion defining an opening for receiving the sample a closed, lower portion comprising a cavity for containing the sample and a reservoir containing a reagent, the reservoir comprising a pierceable membrane;
   a cap, the cap and upper portion of the container each comprising complementary threads configured to removably engage the cap with the container to form a seal, the cap further comprising first engagement means, wherein the first engagements means comprises a first plurality of teeth; and
   an insert configured to nest within the container, the insert comprising an upper portion defining an upper opening, the upper portion of the insert comprising second engagement means complementary to the first engagement means, wherein the second engagement means comprises a second plurality of teeth and wherein the first plurality of teeth are configured to engage with the second plurality of teeth; and
   a lower portion defining a lower opening, the lower portion comprising one or more piercing elements; the insert being open and configured to permit the sample to flow unobstructed through the insert;
   the insert being movable from a first position to a second position within the container, wherein when the insert is in the first position, the one or more piercing elements are located above the pierceable membrane; and
   wherein when said apparatus is sealed by twisting the cap onto the container and engaging the complementary threads, the first plurality of teeth of the first engagement means engage with the second plurality of teeth of the second engagement means causing the insert to rotate and move downward within the container from the first position to the second position, whereby the one or more piercing elements disrupt the pierceable membrane to allow fluid communication between the cavity and the reservoir.

2. The apparatus of claim 1, wherein the cap comprises a top portion and a skirt, the complementary threads comprise internal threads on the skirt configured to engage with external threads provided on the upper portion of the container to removably engage the container with the cap when the internal threads are screwed onto the external threads.

3. The apparatus of claim 1, wherein the first engagement means extend from an underside portion of the cap into an interior of the cap.

4. The apparatus of claim 1, wherein the lower portion of the insert comprises a plurality of piercing elements and a lower peripheral edge of the insert comprises a serrated edge.

5. The apparatus of claim 1, wherein the insert further comprises an annular groove defined on an exterior surface of the insert, and the container comprises a peripheral retaining lip extending from an interior surface of the upper portion of the container, wherein the retaining lip is configured to be received within the annular groove of the insert.

6. The apparatus of claim 1, further comprising a funnel configured to be placed over or be received within the upper portion of the container, wherein the funnel has an upper open end for receiving a sample and a lower open end in fluid communication with the container.

7. The apparatus of claim 1, wherein the container is a tube.

8. The apparatus of claim 7, wherein the tube comprises a false bottom extending from the lower portion of the tube.

9. The apparatus of claim 1, wherein the reagent is a preservative reagent.

10. The apparatus of claim 9, wherein the preservative reagent is a DNA preservative reagent and/or an RNA preservative reagent.

11. The apparatus of claim 1, wherein the reservoir comprises a capsule, the capsule comprising a cavity for containing a reagent and an opening which is sealed with the pierceable membrane, and wherein the capsule is configured to be received in the lower portion of the container.

12. The apparatus of claim 11, wherein the capsule comprises a skirt extending from a peripheral edge of the capsule and the container comprises a first peripheral retaining lip extending from an interior surface of the lower portion of container, wherein the skirt of the capsule is configured to abut the first peripheral retaining lip.

13. The apparatus of claim 12, wherein the capsule further comprises an annular groove defined on an exterior surface of the capsule, and the container comprises a second peripheral retaining lip extending from an interior surface of the lower portion of the container, wherein the second peripheral retaining lip is configured to be received within the annular groove of the capsule.

14. A method for collecting and combining a sample with a reagent, the method comprising:
providing the apparatus of claim 1;
adding a sample into the container; and
closing said container by removably engaging the cap with the container, whereby said insert is moved downward within the container from the first position to the second position, disrupting the pierceable membrane to expose the sample to the reagent.

15. The method of claim 14, wherein the sample is a biological sample.

16. The method of claim 15, wherein the biological sample is a liquid biological sample, which is a blood, plasma, serum, urine, fecal matter, tears, sweat, saliva, breast milk, amniotic fluid, seminal fluid, cerebral spinal fluid, or colostrum sample.

17. The method of claim 15, wherein the biological sample is a solid biological sample, which is a tissue sample or a stool sample.

18. The method of claim 14, wherein the pierceable membrane of the reservoir is substantially removed from the reservoir by the one or more piercing elements.

19. The method of claim 18, wherein the reagent is a preservative reagent.

20. The method of claim 19, wherein the preservative reagent is a DNA preservative reagent and/or an RNA preservative reagent.

21. A kit for collecting and combining a sample with a reagent, the kit comprising: the apparatus of claim 1; and instructions for the use thereof.

22. The kit of claim 21, wherein the reagent is a DNA preservative reagent and/or an RNA preservative reagent and wherein the kit further comprises a funnel for collecting a saliva sample.

23. The kit of claim 21, wherein the reagent is a DNA preservative reagent and/or an RNA preservative reagent and wherein the kit further comprises a stool sample collecting device, wherein the stool collecting device is a spoon or a spatula.

* * * * *